(12) United States Patent
Van De Water et al.

(10) Patent No.: US 8,420,614 B2
(45) Date of Patent: Apr. 16, 2013

(54) COMPOSITIONS AND METHODS FOR INHIBITING OR REVERSING FIBROTIC DISORDERS

(75) Inventors: Livingston Van De Water, Old Chatham, NY (US); Ganary Dabiri, Albany, NY (US); Christopher E. Turner, Chittenago, NY (US)

(73) Assignee: Albany Medical College, Albany, NY (US)

( * ) Notice: Subject to any disclaimer, the term of this patent is extended or adjusted under 35 U.S.C. 154(b) by 318 days.

(21) Appl. No.: 12/527,307

(22) PCT Filed: Feb. 15, 2008

(86) PCT No.: PCT/US2008/054173
§ 371 (c)(1),
(2), (4) Date: May 26, 2010

(87) PCT Pub. No.: WO2008/101219
PCT Pub. Date: Aug. 21, 2008

(65) Prior Publication Data
US 2010/0292300 A1 Nov. 18, 2010

Related U.S. Application Data

(60) Provisional application No. 60/890,210, filed on Feb. 16, 2007.

(51) Int. Cl.
*C12N 15/11* (2006.01)
(52) U.S. Cl.
USPC ...................................................... 514/44 A
(58) Field of Classification Search ................. 514/44 A
See application file for complete search history.

(56) References Cited

U.S. PATENT DOCUMENTS

2002/0094956 A1* 7/2002 Cosgrove ........................ 514/12
2008/0255181 A1* 10/2008 Oh et al. ........................ 514/297

OTHER PUBLICATIONS

Dabiri et al. Molecular Biology of the Cell (2006) vol. 17 (suppl), L13. (Late Abstracts, 46th Annual Meeting of the American Society for Cell Biology).*
Nishiya et al. Molecular and Cellular Biology 2001, p. 5332-5345.*
Roberts et al: "Smad3 is key to TGF-beta-mediated epithelial-to-mesenchymal transition, fibrosis, tumor suppression and metastasis" Cytokine and Growth Factor Reviews, Oxford, GB, vol. 17, No. 1-2, Feb. 1, 2006, pp. 19-27, XP005259964.
Shibanuma M et al: "Characterization of TGF beta 1-inducible hic-5 gene that encodes a putative novel zinc finger protein and its possible involvement in cellular senescence." The Journal of Biological Chemistry Oct. 28, 1994. vol. 269, No. 43, Oct. 28, 1994, pp. 26767-26774, XP009105511.
Dabiri Ganary et al: "TGF-beta1 slows the growth of pathogenic myofibroblasts through a mechanism requiring the focal adhesion protein, Hic-5." The Journal of Invvestigative Dermatology Feb. 2008, vol. 128, No. 2, Feb. 2008, pp. 280-291, XP009105294.
Dabiri G, Tumbarello DA, Turner CE, Van De Water, L.: "Hic-5 Promotes the Hypertrophic Scar Myofibroblast Phenotype by Regulating the TGF-beta1 Autocrine Loop" J Invest Dermatol, vol. online, Apr. 10, 2008, XP002495050, pp. 1-8.
Tumbarello David A et al: "Hic-5 contributes to epithelial-mesenchymal transformation through a PhoA/ROCk-dependent pathway" Journal of Cellular Physiology, vol. 211, No. 3, Jun. 2007, pp. 736-747, XP002492051.
The International Search Report for PCT/US2008/054173, dated Sep. 10, 2008.

* cited by examiner

*Primary Examiner* — Brian Whiteman
(74) *Attorney, Agent, or Firm* — Heslin Rothenberg Farley & Mesiti P.C.

(57) ABSTRACT

The present invention provides compositions and methods for inhibiting or reversing fibrotic disorders by administering a Hic-5 antagonist to a mammal in need thereof. The invention also includes methods for screening compounds to identify Hic-5 antagonists useful in inhibiting or reversing fibrotic disorders.

1 Claim, 17 Drawing Sheets

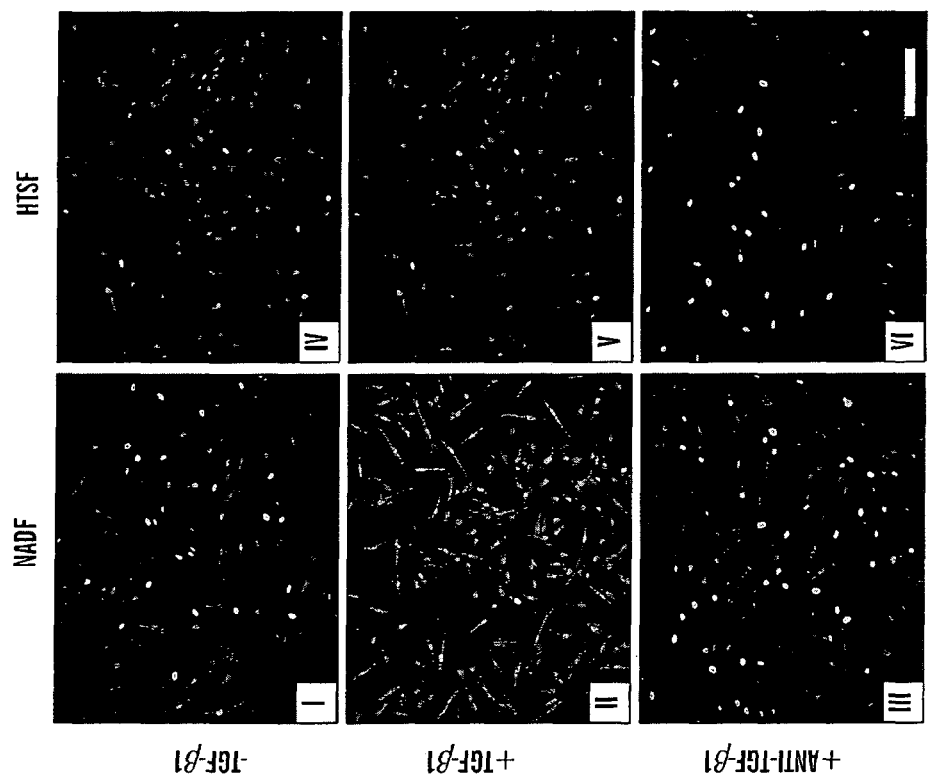
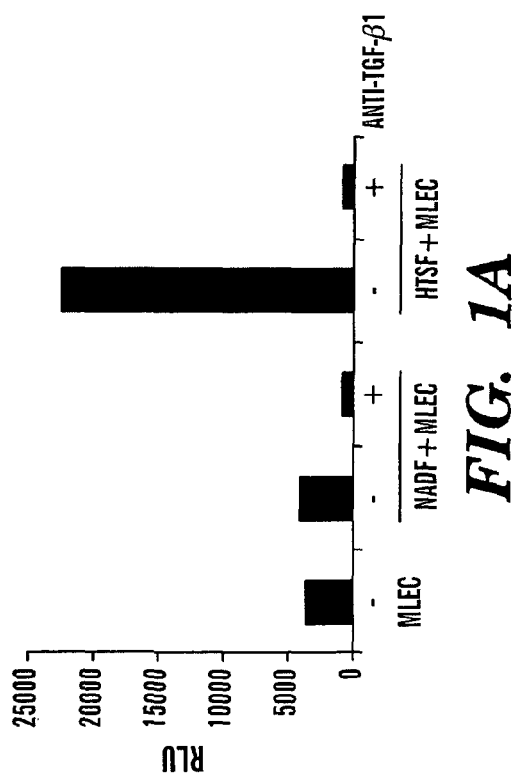
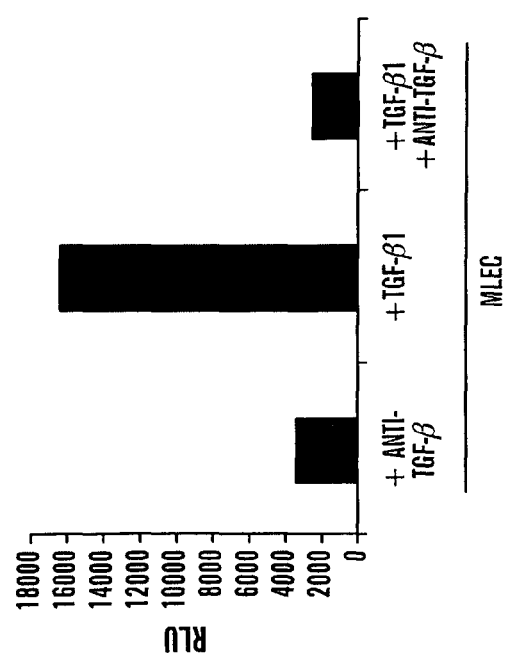
FIG. 1D
FIG. 1A
FIG. 1B

COMPOSITIONS AND METHODS FOR INHIBITING OR REVERSING FIBROTIC DISORDERS

CROSS REFERENCE TO RELATED APPLICATIONS

This application is a 371 filing of PCT International application no. PCT/US2008/054173 filed Feb. 15, 2008 and published in English as WO 2008/101219 on Aug. 21, 2008, which claims the priority of U.S. Provisional application No. 60/890,210 filed Feb. 16, 2007. The disclosures of these applications and all other patents, published applications and other references cited herein are hereby incorporated by reference in their entirety.

STATEMENT OF FEDERALLY SPONSORED RESEARCH

This invention was made with government support under Grant Nos. GM-56442 and GM-47607 awarded by National Institutes of Health. The U.S. government has certain rights in the invention.

BACKGROUND OF THE INVENTION

1. Field of the Invention

The present invention relates to compositions and methods for inhibiting and reversing fibrotic disorders by blocking expression of the focal adhesion protein hydrogen peroxide inducible clone-5 (Hic-5), which is shown herein to be essential for perpetuating the decreased proliferation of myofibroblasts derived from hypertrophic scar fibroblasts and for regulating the autocrine production of TGF-beta.

2. Description of the Related Art

Scar formation, whether normal or pathogenic, is driven by myofibroblasts, a cell type differentiated from quiescent fibroblasts in a process that requires TGFβ1 and mechanical stress. Pathogenic fibrosis comprises a constellation of diseases in which the excessive and chronic deposition of scar proteins reduces organ functions, impairs joint mobility and compromises psychological well-being. It is generally understood that the onset of cutaneous fibrosis occurs due to the over stimulation and robust differentiation of fibroblasts into myofibroblasts during wounding leading to excess collagen deposition, hyperplasia, and excessive scar deposition and contraction. While myofibroblast differentiation during normal acute wound healing is temporally limited, in fibrotic settings these myofibroblasts persist in relatively high numbers for long periods following injury. However, the mechanisms controlling fibroblast activation and differentiation, and the persistence of myofibroblasts are still largely unknown. Certainly, it has been shown that TGFβ1 is the major cytokine responsible for the onset of fibrotic disorders such as keloids, Dupuytren's disease, and hypertrophic scars. Yet factors other than TGFβ, such as the composition of the extracellular matrix (ECM) and the mechanical environment are also important. Pathogenic scarring is a devastating disorder that impairs normal tissue function following injury. One type of pathogenic scarring, hypertrophic scars (HTS), develop after injury to the deep dermis usually following thermal injury or surgery. Histological examination of HTS shows distinct nodules that contain an excessive number of fibroblasts along with myofibroblasts, small vessels, and fine collagen fibers that are arranged parallel to the surface of the skin. Clinical examination shows that HTS tend to be erythematous, pruritic, thick, and raised. However unlike keloids, HTS remain within the boundary of the original trauma site. Treatment options for HTS are available but can be limited and are not always cosmetically favorable. Therefore, the mechanism involved in the development of HTS needs to be established in order to prevent its formation.

Fibroblasts play an important role in the wound healing process. They migrate to the wound bed in response to various growth factors, such as TGFβ and PDGF, and proliferate, differentiate, and lay down a new ECM containing collagen and fibronectin (44). Fibroblasts bind to these ECM proteins via focal adhesions which contain integrins that link the extracellular matrix to the actin filament inside the cell via anchoring proteins such as vinculin, talin, paxillin, and α-actinin. The transition from fibroblast to myofibroblast is likely due to the combined action of three different agents: mechanical tension, TGFβ1, and possibly the splice variant EIIIA, also termed ED-A, of cellular fibronectin. Blocking the EIIIA domain of cellular fibronectin has been reported to inhibit α-SMCA and collagen type I mRNA induction by TGFβ1 in myofibroblasts. Fibroblasts that express α-SMCA, termed myofibroblasts, are critical for wound contraction and its subsequent closure. However, excessive contraction by this cell type is an important component of hypertrophic scarring. As a model of wound contracture, the dynamic process of wound closure can be broken down into two major components: focal adhesions binding to the ECM; and alpha smooth muscle actin insertion into these adhesion sites. Once assembled, these mature adhesions may then pull the wound closed. Dugina et al in 2001 categorized the large, more mature, adhesions as supermature focal adhesions (>6 μm$^2$). Differentiated myofibroblasts deposit and organize scars over a continuum, from normal to pathogenic, and yet the mechanisms regulating their appearance and disappearance from tissues are enigmatic.

Hypertrophic Scars. When skin is injured, there is a cascade of mechanisms that occur in order to close the open wound, which ultimately leads to scar. The resulting scar, regardless of cause, leaves a permanent reminder of the injury. This is especially true of one type of fibrotic disorder, hypertrophic scars (HTS), which are aggressively healing wounds that occur after an injury to the skin usually following thermal injury or injury to the deep dermis. HTS represent a form of wound healing in which scarring is exaggerated. While at most sites this is primarily of cosmetic concern; some hypertrophic scars can cause significant loss of movement if contractures occur at sites overlying a joint. HTS can also result in significant disfigurement if located on the face. HTS tend to be thick, erythematous, raised and can be painful or pruritic. Nonetheless, the scar remains within the boundary of the original trauma site and can occur in all racial or ethnic groups. Histological examination of HTS shows distinct nodules that contain fine collagen fibers and an excessive number of alpha smooth muscle cell actin (SMCA)-positive fibroblasts (Ehrlich et al., 1994). These characteristics are perpetuated by the autocrine production and activation of TGF-β1 (Scott et al., 2000; Tomasek et al., 2002). Because large numbers of myofibroblasts persist in these nodules, it is widely believed that these cells are hyperproliferating, hence, its characterization in the literature as a fibroproliferative disorder (Tredget et al., 1997). Regression of the scar occurs after 12-18 months, unfortunately, the scar never fully resolves. To improve the cosmetic appearance of the HTS a variety of treatment options are available including: surgery, radiation therapy, pressure, silicone dressings, laser surgery, corticosteroids, cryotherapy, and interferon. Unfortunately, the options available are neither completely effective nor do they work for all patients.

Cutaneous Wound Healing. The wound healing process can be divided into 4 distinct but overlapping phases: Coagulation, inflammation, proliferation, and remodeling. Immediately following tissue injury the initial response is usually bleeding, followed by hemostasis, and then scab formation. Within the first 6-8 hours, the next phase of the healing process (inflammation) is underway. Transforming Growth Factor Beta (TGFβ), secreted from the degranulated platelets is among the growth factors and cytokines that attract polymorphonuclear leukocytes (PMNs) to clear the wound site where they kill and remove microorganisms. As the process continues, monocytes also migrate to the wound and undergo differentiation into activated macrophages. The macrophages serve multiple functions including phagocytosis of bacteria, dead neutrophils, and tissue debris. Importantly, they also secrete various growth factors during the first several days including Transforming growth factors (TGF), vascular endothelial growth factor (VEGF), interleukin-1 (IL-1), insulin like growth factor (IGF), and platelet derived growth factor (PDGF). In doing so, macrophages are instrumental in the formation of granulation tissue.

During the third stage of wound healing, termed the proliferative phase, epithelialization, angiogenesis, granulation tissue formation, and tissue remodeling occur. Reepithelialization begins hours after wounding and is completed within several days. Clotted blood and damaged extracellular matrix (ECM) are removed by epidermal cells along the migration pathway by their secretion of matrix metalloproteinases (MMPs), and plasmin. Migrating epidermal cells also loosen both cell-cell adhesive sites and hemidesmosomes aiding in the lateral movement of these cells into the wound bed.

Angiogenesis is a complex process involving the interplay of factors such as growth factors, cytokines, and ECM. Angiogenesis occurs as an orderly cascade of molecule and cellular events in the wound bed. The angiogenic process is characterized by complex growth factor-receptor, cell-cell, and cell-matrix interactions. Angiogenic growth factors bind to their receptors on the surface of endothelial cells activating a cascade of signaling activities. These activated endothelial cells release proteolytic enzymes that dissolve the basement membrane. Endothelial cells migrate to the wound bed using integrins αvβ3, αVβ5, and α5β1. Sprouting vessels begin to form and these vessels form tubular channels which connect to form vascular loops. New blood vessels mature and blood flow begins.

Tissue remodeling is a process in which fibroblasts deposit collagen to form a scar. By day 4, fibroblasts, in response various growth factors such as TGFB and PDGF, migrate into the wound bed, proliferate, differentiate, and deposit a new ECM. Early in normal wound healing, type III collagen predominates but later type I collagen is more prevalent than type III. The differentiation of fibroblasts into myofibroblasts occurs during granulation tissue formation and is driven by TGFβ and potentially the EIIIA segment of fibronectin (FN). Myofibroblasts which resemble contractile smooth muscle cells have been shown to be critical in the process of wound contraction. These contractile cells also elaborate large focal adhesions. The wound undergoes constant alterations known as remodeling, which start during the first week after injury and can continue for years after the initial injury occurred. During the remodeling phase of normal wounds, collagen is degraded and deposited in an equilibrium fashion generally resulting in no change in the amount of collagen present in the wound.

Deregulated Wound Healing. The wound healing process, specifically the last two phases, can go awry and excessive scarring (fibrosis) occurs. TGFβ stimulates fibroblasts to produce ECM proteins such as collagen, cellular fibronectin, glycosaminoglycans, and elastin. In HTS there is an increase in the expression of types I and type III procollagen mRNA and protein and a decrease in collagenase which disrupts the collagen degrading and deposited equilibrium. Histological examination of HTS shows distinct nodules that contain an excessive number of fibroblasts along with myofibroblasts, small vessels, and fine collagen fibers that are arranged parallel to the surface of the skin, and are oriented along the tension line of the scar. Pathogenic skin contracture likely results from excessive contraction and reorganization of the ECM by myofibroblasts in the wound and may contribute to the clinical observation that HTS are raised and thick.

Focal Adhesion Formation. As described above, fibroblasts play a central role in the wound healing process. Fibroblasts are responsible for the production of ECM proteins and for contraction of the wound. This latter process clearly involves tight adhesions to the ECM and yet the mechanisms through which this occurs are unclear. Focal adhesions, rich in integrins, are likely critical because they link the outside of the cell to the actin filament inside the cell via anchoring proteins such as vinculin, talin, paxillin, and α-actinin. In resting cells, these integrins are located on the ventral surface of the cell and are not clustered. The actin filaments associated with these integrins are under little or no tension, because the myosin II is in its inactive conformation.

The process of focal adhesion formation is governed by the Rho family GTPases which are members of the Ras superfamily of low molecular weight GTP-binding proteins. Rho regulates the formation of stress fibers and focal adhesions, Rac regulates the extension of lamellipodia, large sheet-like extensions filled with a network of actin filaments and induces focal complex formation, and cdc42 stimulates the formation of filopodia, fingerlike extensions from the cell that contain a core of bundled actin filaments. Focal adhesions arise from focal complexes which are formed at the cell periphery in a Rac dependent process. Focal complexes contain the same proteins but are generally much smaller and more transient then focal adhesions. Rottner et. al. showed that the transition of focal complexes associated with the lamellipodia, to focal adhesions associated with stress fiber bundles is effected by a change in the balance of signaling, from Rac to Rho. They injected a constitutively active Rho mutant (L63Rho) to up regulate Rho activity this caused a transition of the Rac-induced focal complexes at the periphery of the cell into larger, elongated adhesions, corresponding to Rho-induced focal adhesions. They also showed that when the Rho-kinase inhibitor (Y-27632) was added to inhibit the downstream pathway of Rho that leads to focal adhesion assembly, it caused the rapid disassembly of the focal adhesions. In addition, the cell actively initiated the formation of lamellipodia and associated focal complexes, diagnostic of the activation of Rac. These experiments showed that focal complexes likely serve as precursors of focal adhesions.

The activation of Rho by GTP binding leads to myosin light chain phosphorylation and promotes myosin filament assembly and subsequently alignment of the actin filaments. The tension generated is transmitted to the integrins in the membrane, leading to their aggregation. This clustering of integrins is the foundation of focal complex and focal adhesion assembly. Conversion of focal complexes to focal adhesions is dependent on the development of mechanical stress in the actin cytoskeleton.

In 2001, Dugina et. al. defined focal adhesions based on size, as either immature (area≦2 µm$^2$), mature (area=2-6 µm$^2$) and supermature (area≧6 µm$^2$). All of these adhesions were connected to actin bundles, however, supermature adhesions were only connected to stress fibers that contained αSMCA.

Hic-5 is a TGF-β-inducible and $H_2O_2$-inducible focal adhesion protein that shuttles to the nucleus where it may serve as a transcription factor (Shibanuma et al., 1994). Hic-5 is also a focal adhesion LIM-containing protein with homology to paxillin and can interact with FAK and vinculin (Thomas et al., 1999). Hic-5 includes four LD domains in its N-terminal half and four LIM domains in its C-terminal half with a nuclear export signal (NES) in LD3 (Brown and Turner 2004). Hic-5 accumulates in the nucleus in response to oxidants, such as $H_2O_2$, and it can shuttle between focal adhesions and the nucleus through an oxidant-sensitive NES (Shibanuma et al., 2003). Hic-5 is likely retained in the nucleus through a mechanism requiring all four LIM domains that serve as an unconventional nuclear localization sequence (Shibanuma et al., 2003). In the nucleus, Hic-5 participates in the transcriptional control of genes including c-fos and p21 (Shibanuma et al., 2004). Hic-5 is also markedly upregulated during the TGF-β-induced, epithelial-mesenchymal transition (EMT) (Tumbarello and Turner, in press).

Fibronectin. Fibronectins (FN) are a family of glycoproteins that are prominent components of the ECM of wounds and exists in two main forms: An insoluble glycoprotein dimer that serves as a linker in the ECM (cellular FN) and as a soluble disulphide linked dimer found in the plasma (plasma FN) which can assemble into the insoluble matrix. The plasma form is synthesized by hepatocytes, and the cellular form is synthesized by fibroblasts among other cell types. Cellular fibronectin contains a series of homologous repeats of three different types (FN I, FN II, FN III). Fibronectin exhibit molecular heterogeneity arising from post translational modification and alternative splicing at three different regions termed EIIIA (EDA), EIIIB (EDB) and IIICs. As a result of alternative splicing the EIIIA and EIIIB region are either included or excluded due to tissue specificity or during embryogenesis at different stages of development. EIIIA and EIIIB segment may regulate processes such as cell adhesion, migration, and spreading. EIIIA potentates the ability of FN to promote cell cycle progression. During wound healing the plasma fibronectin that is extravagated following injury is replaced by the local synthesis of cellular FNs by macrophages and fibroblasts. In cutaneous wound healing the EIIIA portion my also be important for normal re-epithelization.

Transforming Growth Factor Beta. Transforming growth factor beta (TGFβ) is a potent cytokine that inhibits the growth of several types of cells and has been shown to be both pro-proliferative and anti-proliferative for fibroblasts. TGFβ is a member of a large superfamily of polypeptide growth factors and regulates many different types of cellular processes, such as embryonic development, growth inhibition, proliferation, cell differentiation, cell adhesion, cell migration, wound healing, apoptosis, and immunosuppression. It tightly regulates the production of ECM proteins such as fibronectin, collagen, and plasminogen activator inhibitor-1 (PAI-1). During wound healing, TGFβ is released from degranulating platelets and many of the participating cells in wound healing (fibroblasts, keratinocytes, inflammatory cells, and endothelial cells) can both produce and respond to TGFβ during the course of the healing process.

There are three isoforms of TGFβ: TGFβ1, TGFβ2, and TGFβ2. They are all 25 kDa homodimers. All TGFβs are synthesized as dimeric precursor proproteins that are cleaved within by the Golgi Apparatus to remove the pro-peptide. The carboxy terminal fragment which contains the mature TGFβ remains associated non-covalently with its amino terminal propeptide called latency-associated protein (LAP). For stabilization and correct folding of secreted latent TGFβ, LAP is bound by disulfide bonds to the latent TGFβ binding protein (LTBP), resulting in a large latent complex (LLC), which is targeted to the ECM for storage. A conformational change to the LLC complex by thrombospondin-1 (TSP-1) or plasmin results in the dissociation of LAP leading to the activation of TGFβ. Recent data also implicates integrin αvβ6 in the process of TGFβ activation.

Active TGFβ signals through transmembrane receptor serine/threonine kinases that activate a family of cytoplasmic proteins called Smads, which translocate into the nucleus to regulate expression of target genes. In addition to Smad proteins, G proteins and MAPKs are also involved in the downstream signaling of TGF-β family members (Moustakas and Heldin 2005). The growth inhibitory pathway of TGF-β1 is mediated through Smad-independent and -dependent mechanisms, through which the expression of the cell-cycle inhibitors $p21^{cip1}$, $p27^{kip1}$, and $p15^{ink4b}$ is regulated (Hu et al., 1998). The TGFβ family receptors are divided into three groups, known as the type I, and type II and type III receptors. The type I and type II transforming growth factor beta receptors (TβR) are signaling receptors whereas the type III receptor regulates the accessibility of TGFβ to the signaling receptors. The type II receptor is constitutively active and upon active TGFβ binding to the TβRII receptor, the TβR-1 is recruited and forms a heterotetrameric complex. The formation of the heterotetrameric complex results in the activation of the TβR-1 through phosphorylation at the serine and threonine residues. The active TβR-1 subsequently phosphorylates members of the Smad signaling pathway. The Smad proteins are prominent components of the signaling pathway downstream of the TGFβ receptors. The Smad family consists of proteins with molecular masses of 42 kDa-65 kDa. Smads are categorized into three subgroups: R-Smads (receptor activated Smads), Co-Smads (Smads that associate with the R-Smads called common partner Smads), and the I-Smads (inhibitory Smads that block the signaling function of the first two subfamilies). In order for the Smad proteins to be activated by the TGFβ receptor, they need to come in closer proximity to the activated receptor. Proteins such as SARA (Smad anchor for receptor activation), help present Smad 2 and 3 (no other R-Smad) to TβR-1. Phosphorylation of the complex causes decreased binding affinity to SARA and an increased binding affinity to Smad4. TRAP-1 (TGFβ receptor associated protein) is bound to the inactive TβR-1 and upon receptor activation, TRAP-1 dissociates from TβR-1 and interacts with Smad4, thereby facilitating Smad4 binding to the phosphorylated Smad2 or Smad3 which then translocates into the nucleus and affects transcription by binding to specific gene promoters and recruitment of transcription factors. TGFβ1 is a major player in the wound healing process, in part because it is central to the control of fibroblast differentiation discussed above. Different human diseases such as fibrosis, multiple sclerosis, vascular diseases, Parkinson's disease, Alzheimer's disease, autoimmune diseases, and cancer have been implicated in deregulated TGFβ signaling. TGFβ1 has been implicated as the major cytokine responsible for the onset of fibrotic disorders such as keloids, Dupuytren's disease, and hypertrophic scars.

Since TGFβ1 is the major cytokine involved in fibroblast differentiation to myofibroblast and these myofibroblast cells are responsible for wound contracture, it is necessary to study the effect that TGFβ1 has on the induction of super mature focal adhesions and the binding effect these larger adhesions have on ECM that aid in the over contracture of the healing wound resulting in a hypertrophic scar.

It has been estimated that up to 45% of deaths in the United States can be attributed to fibroproliferative diseases, which can affect many tissues and organ systems. (Wynn, supra, at 595 (2004)). Major organ fibrotic diseases include interstitial lung disease (ILD), characterized by pulmonary inflammation and fibrosis. ILD is known to have a number of causes such as sarcoidosis, silicosis, collagen vascular diseases, and systemic scleroderma. However, idiopathic pulmonary fibrosis, a common type of ILD, has no known cause. Other organ fibrotic disorders include liver cirrhosis, liver fibrosis resulting from chronic hepatitis B or C infection, kidney disease, heart disease, and eye diseases including macular degeneration and retinal and vitreal retinopathy. Fibroproliferative disorders also include systemic and local scleroderma, keloids and hypertrophic scars, atherosclerosis, and restenosis. Additional fibroproliferative diseases include excessive scarring resulting from surgery, chemotherapeutic drug-induced fibrosis, radiation-induced fibrosis, and injuries and burns (Wynn, supra, page 585). All tissues damaged by trauma are prone to scar and become fibrotic, particularly if the damage is repeated.

Currently, treatments are available for fibrotic disorders including general immunosuppressive drugs such as corticosteroids, and other anti-inflammatory treatments. However, the mechanisms involved in regulation of fibrosis appear to be distinctive from those of inflammation, and anti-inflammatory therapies are not always effective in reducing or preventing fibrosis (Wynn, supa, page 591).

Applicants have overcome or alleviated a problem of the prior art by discovering that a known focal adhesion protein, Hic-5, plays an important role in the maintenance of pathogenic fibroblasts, which when knocked down by siRNA or inhibited pharmacologically results in the reversion of pathogenic myofibroblasts to a more normal fibroblast phenotype, and thus, serves as an important new target for inhibiting and reversing fibrotic disorders.

RELATED ART CITATIONS

Throughout the instant specification, reference has been made to various patent and/or scientific literature references, some of which appear below. The disclosures of these publications in their entireties are hereby incorporated by reference as if written herein. No admission is made as to the status of any of these references as prior art.

Abe M, Harpel J, Metz C N, Nunes I, Loskutoff D J, Rifkin D B (1994). An assay for TGF-β using cells transfected with a plasminogen activator inhibitor-1 promoter-luciferase construct. Anal Biochem 216: 276-284.

Brown M C, Turner C E (2004). Paxillin: adapting to change. Physiol Rev 84: 1315-1339.

Campaner A B, Ferriera L, Gragnani A, Bruder J M, Cusick J L, Morgan J R (2006). Upregulation of TGF-β1 expression may be necessary but is not sufficient for excessive scarring. J Invest Dermatol 126: 1168-1176.

Dabiri G, Campaner A, Morgan J R, Van De Water L (2006). A TGF-β1-dependent autocrine loop regulates the structure of focal adhesions in hypertrophic scar fibroblasts. J Invest Dermatol 126: 963-970.

Desmouliere A, Redard M, Darby I, Gabbiani G (1995). Apoptosis mediates the decrease in cellularity during the transition between granulation tissue and scar. Am J Pathol 146: 56-66.

Ehrlich H P, Desmouliere A, Diegelmann R F, Cohen I K, Compton C C, Garner W L, et al (1994). Morphological and Immunochemical differences between keloid and hypertrophic scar. Am J Pathol 145: 105-113.

Feng X H, Derynck R (2005). Specificity and versatility in TGF-β1 signaling through Smads. Annu Rev Cell Dev Biol 21: 659-693.

Grinnell F (1994). Fibroblast, myofibroblast, and wound contraction. J Cell Bio 124: 401-404.

Hagmann J, Grob M, Welman A, Van Willigen G, Burger M M (1998). Recruitment of the LIM protein hic-5 to focal contacts of human platelets. J Cell Sci 111: 2181-2188.

Hu P P, Datto M, Wang X F. (1998) Molecular mechanisms of TGF-β1 signaling. Endocr Rev 19: 349-363.

Huang S S, Huang J S (2005). TGF-beta control of cell proliferation. J Cell Biochem 96: 447-462.

Lal B K, Saito S, Pappas P J, Padberg F T Jr, Cerveira J J, Hobson R W 2nd, et al (2003). Altered proliferative responses of dermal fibroblasts to TGF-β1 may contribute to chronic venous stasis ulcer. J Vasc Surg 37: 1285-93.

Moulin V, Langlois S, Langlois C, Thibault I, Lopez-Valle C A, Roy M (2004). Normal skin wound and hypertrophic scar myofibroblasts have differential responses to apoptotic inductors. J Cell Physiol 198: 350-358.

Moustakas A, Heldin CH (2005). Non-Smad TGF-β signals. J Cell Sci 118: 3573-3584.

Ravitz M J, Wenner C E. (1997). Cyclin-dependent kinase regulation during G1 phase and cell cycle regulation by TGF-β1. Adv Cancer Res 71: 165-207.

Roberts A B, Tian F, Byfield S D, Stuelten C, Ooshima A, Saika S, et al (2006). Smad3 is key to TGF-β1 mediated epithelial-to-mesenchymal transition, fibrosis, tumor suppression and metastasis. Cytokine Growth Factor Rev 17: 19-27.

Scott P G, Ghahary A, Tredget E E. (2000). Molecular and cellular aspects of fibrosis following thermal injury. Hand Clin 16: 271-287.

Shibanuma M, Kim-Kaneyama J, Ishino K, Sakamoto N, Hishiki T, Yamaguchi K, et al (2003). Hic-5 communicates between focal adhesions and the nucleus through oxidant-sensitive nuclear export signal. Mol Biol Cell 14: 1158-1171.

Shibanuma M, Kim-Kaneyama J, Sato S, Nose K. (2004). A LIM protein, Hic-5, functions as a potential coactivator for Sp1. J Cell Biochem 91: 633-645.

Shibanuma M, Mashimo J, Kuroki T, Nose K (1994). Characterization of the TGF-β-inducible hic-5 gene that encodes a putative novel zinc finger protein and its possible involvement in cellular senescence. J Biol Chem 269: 26767-26774.

Singer A J, Clark R (1999). Cutaneous wound healing. N Engl J Med 341: 738-746.

Thomas S M, Hagel M, Turner C E (1999). Characterization of a focal adhesion protein, Hic-5, that shares extensive homology with paxillin. J Cell Sci 112: 181-190.

Thornton S C, Por S, Walsh B J, Penny R, Breit S N (1990). Interaction of immune and connective tissue cells: The effect of lymphokines and monokines on fibroblast growth. J Leukoc Biol 47: 312-320.

Tomasek J J, Ghahary G, Hinz B, Chaponnier C, Brown R A (2002). Myofibroblasts and mechano-regulation of connective tissue remodeling. Nat Rev Mol Cell Biol 3: 349-363.

Tredget E E, Nedelec B, Scott P G, Ghahary A (1997). Hypertrophic scars, keloids, and contractures. The cellular and molecular basis for therapy. Surg Clin North Am 77: 701-730.

Tredget E E, Wang R, Shen Q, Scott P G, Ghahary A (2000). TGF-β mRNA and protein in hypertrophic scar tissues and fibroblasts: antagonism by IFN-alpha and IFN-gamma in vitro and in vivo. J Interferon Cytokine Res 20: 143-151.

Tumbarello D A, Brown M C, Hetey S E, Turner C E (2005). Regulation of paxillin family members during epithelial-mesenchymal transformation: a putative role for paxillin delta. *J Cell Sci* 118: 4849-4863.

Yuminamochi T, Yatomi Y, Osada M, Ohmori T, Ishii Y, Nakazawa K, et al (2003). Expression of the LIM proteins paxillin and Hic-5 in human tissues. *J Histochem Cytochem* 51: 513-521.

Zhang H Y, Phan S (1999) Inhibition of myofibroblast apoptosis by TGF-β1. *Am J Respir Cell Mol Biol* 21: 658-665.

Blobe G, Schiemann W, Lodish H (2000) Role of transforming growth factor β in human disease. *New Eng J Med* 342:1350-1358.

Dabiri G, Tumbarello D, Turner C, Van De Water L (2007) TGF-β1 slows the growth of pathogenic myofibroblasts through a mechanism requiring the focal adhesion protein, Hic-5. *J Invest Dermatol* August 2; [Epub ahead of print]; PMID: 17671518.

Desmoulière A, Geinoz A, Gabbiani F, Gabbiani G (1993) Transforming growth factor-β1 induces α-smooth muscle actin expression in granulation tissue myofibroblasts and in quiescent and growing cultured fibroblasts. *J Cell Biol* 122:103-111.

Hinz B (2007) Formation and function of the myofibroblast during tissue repair. *J Invest Dermatol* 127:526-537.

Kim-Kaneyama J, Shibanuma M, Nose K (2002) Transcriptional activation of the c-fos gene by a LIM protein, Hic-5. *Biochem Biophys Res Commun* 299:360-365.

Shibanuma M, Mochizuki E, Maniwa R, Mashimo J, Nishiya N, Imai S, et al. (1997) Induction of senescence-like phenotypes by forced expression of hic-5, which encodes a novel LIM motif protein, in immortalized human fibroblasts. *Mol Cell Biol* 17:1224-1235.

Tuan T, Nichter T (1998) The molecular basis of keloid and hypertrophic scar formation. *Mol Med Today* 1:19-24.

Tumbarello D, Turner C (2007) Hic-5 contributes to epithelial-mesenchymal transformation through a RhoA/ROCK-dependent pathway. *J Cell Physiol* 211:736-747.

Wynn T (2007) Common and unique mechanisms regulate fibrosis in various fibroproliferative diseases. *J Clin Invest* 117:524-529.

Yang L, Guerrero J, Hong H, DeFranco D, Stallcup M (2000) Interaction of the tau2 transcriptional activation domain of glucocorticoid receptor with a novel steroid receptor co-activator, Hic-5, which localizes to both focal adhesions and the nuclear matrix. *Mol Biol Cell* 11:2007-2018.

Barisic-Dujmovic et al. (2007) Regulation of collagen gene expression in the Tsk2 mouse. *InterScience*: www3.interscience.wiley.com Melov et al. (2001) Lifespan extension and rescue of spongiform encephalopathy in superoxide dismutase 2 Nullizygous mice treated with superoxide dismutase-catalse mimetics. *The Journal of Neuroscience* 21(21):8384-8353.

Abraham et al. (2005) Scleroderma: from cell and molecular mechanisms to disease models. *Trends in Immunonology* 26(11):587-595.

Murata et al. (2003) Therapeutic significance of Y-27632, a Rho-kinase inhibitor on the established liver fibrosis. *The Journal of Surgical Research* 114:64-71.

Saito et al. (2007) Inhibition of NAD(P)H oxidase reduces apoptosis and avascular retina in an animal model of retinopathy or prematurity. *Molecular Vision* 13:840-853.

Wang et al. (2007) Delivery and Inhibition of reporter genes by small interfering RNAs in a mouse skin model. *The Society for Investigative Dermatology* 127:2577-2584.

Oliveira, et al. (2006) Targeted delivery of siRNA. *Journal of Biomedicine and Biotechnology* 2006:1-9.

SUMMARY OF THE INVENTION

Applicants are the first to disclose the surprising discovery that Hic-5 is required to maintain the autocrine loop of TGF-β1 in hypertrophic scar fibroblasts by regulating TGF-β1 production. Thus, Hic-5 is upregulated by TGF-β1 and, in turn, is required for the production of TGF-β1 in a feed-forward mechanism in which TGF-β1 levels remain constitutively high, thereby maintaining the pathogenic myofibroblast phenotype. Applicants have further discovered that Hic-5 is a new target in HTSF, and potentially other pathogenic myofibroblasts, and, when inhibited, can provide therapeutic benefit in the treatment, inhibition, or reversing of cutaneous fibrosis, and other fibrotic disorders.

In accordance with these findings, the present invention provides compositions and methods for inhibiting and reversing a fibrotic disorder by blocking expression of the focal adhesion protein hydrogen peroxide inducible clone-5 (Hic-5), which is shown herein to be essential for perpetuating the decreased proliferation of myofibroblasts derived from hypertrophic scar fibroblasts and for autocrine production of TGF-beta.

In one aspect, methods for inhibiting or reversing a fibrotic disorder in a mammalian subject are provided herein. In an embodiment, the method includes administering a therapeutically effective amount of a composition containing a Hic-5 antagonist and a pharmaceutically effective carrier.

In another aspect, the invention provides methods of screening for an agent capable of inhibiting or reversing a fibrotic disorder by providing an animal with a fibrotic disorder, administering the agent to said animal, and determining the amount of smooth muscle cell α-actin (SMCA) expression over a period of time, wherein a decrease in SMCA expression indicates that the agent inhibits the expression or activity of Hic-5 and is therefore capable of inhibiting or reversing a fibrotic disorder. In an embodiment, the effect of the agent is determined by the change in phenotype, i.e., from pathogenic myofibroblast to normal fibroblast.

In another aspect, the invention provides methods of screening for an agent capable of inhibiting or reversing a fibrotic disorder by exposing a myofibroblast to an agent and determining the effect of the agent on the myofibroblast by determining the amount of smooth muscle cell α-actin (SMCA) expression wherein a decrease in SMCA expression indicates that the agent inhibits the expression or activity of Hic-5 and is therefore capable of inhibiting or reversing a fibrotic disorder.

In an embodiment, the myofibroblast is replaced with a cell that has been genetically engineered to express Hic-5 and a fluorophore such that when the agent activates Hic-5, expression of the fluorphore occurs and is proportional to Hic-5 expression. In one embodiment, the fluorophore is luciferase.

In another aspect, the invention provides methods for regulating the level of an extracellular matrix (ECM) protein or smooth muscle cell actin (SMCA) produced by a cell by modulating expression or activity of the focal adhesion protein, Hic-5.

In yet another aspect, the invention provides methods of inhibiting the TGF-β1 signaling pathway in a patient in need thereof by administering to the patient a composition comprising a therapeutically effective amount of a Hic-5 antagonist and a pharmaceutically acceptable carrier.

In an embodiment, the fibrotic disorder is chosen from pulmonary fibrosis, hepatic fibrosis (cirrhosis), renal fibrosis, corneal fibrosis, heart fibrosis, osteoarticular fibrosis, tissue fibrosis, tumor stroma, desmoplastic tumors, surgical adhesions, hypertrophic scars, and keloids.

In an embodiment, the tissue fibrosis affects a tissue chosen from muscle tissue, skin epidermis, skin dermis, tendon, cartilage, pancreatic tissue, uterine tissue, neural tissue, testis, ovary, adrenal gland, artery, vein, colon, small and large intestine, biliary tract, and gut.

In an embodiment, the fibrotic disorder results from scarring of a wound, hepatitis B or C infection, *Schistosoma* infection, kidney disease, heart disease, macular degeneration, retinal and vitreal retinopathy, systemic and local scleroderma, atherosclerosis, restenosis, chemotherapeutic drug-induced fibrosis, radiation-induced fibrosis, and burns.

In another embodiment, the scarring of a wound results from a puncture wound, a laceration, a surgical incision, an abrasion, a pressure wound, or a burn.

In an embodiment, the Hic-5 antagonist is chosen from Hic-5 siRNA, a combination regimen (Y27632 and apocyanin), and Fe-TBAP. In one embodiment, the Hic-5 siRNA is SEQ ID NO:1 or SEQ ID NO:2.

These and other aspects of the invention will become evident upon reference to the following detailed description of the invention, and accompanying drawings.

BRIEF DESCRIPTION OF THE DRAWINGS

FIGS. 1(A)-(E): Autocrine induction of TGF-β1 results in decreased proliferation in HTSF. (1A) MLEC expressing the PAI-1 luciferase construct were co-cultured with either NADF or HTSF in the presence or absence of anti-TGF-β1 (20 µg/ml) (1B) To test specificity and stoichiometry, MLEC expressing the PAI-1 luciferase construct were incubated with recombinant active TGF-β1 (5 ng/ml) and/or anti-TGF-β1 (10 ng/ml). (1C) Cells were cultured in serum-containing media with or without the addition of exogenous TGF-β1 (10 ng/ml) or anti-TGF-β (20 µg/ml) for 72 hrs and cell growth was determined using CyQUANT® assay (increase in cell number at day 3 is calculated as cell number at day 3 minus cell number at day 0). (1D) Cells were incubated in serum free media for 24 hours, then serum was added and cells were pulsed with BrdU and TGF-β1 (10 µg/ml) or anti-TGF-β (20 µg/ml) for 24 hours. Cells were stained for BrdU (green) and DNA (blue). (1E) Percent positive BrdU was calculated as a ratio: (# blue-green colocalization)/total # blue) multiplied by 100. *$p<0.005$, n=3.

DETAILED DESCRIPTION OF THE INVENTION

Figure 1C:
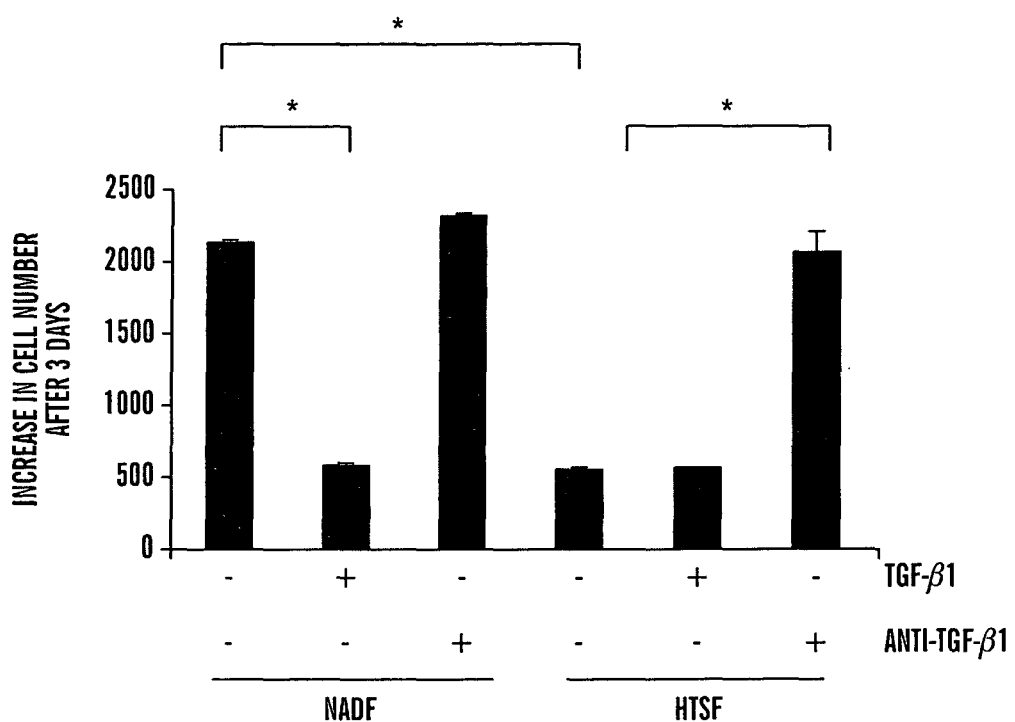

Hic-5 antagonists or inhibitors that specifically block expression or activity of the Hic-5 gene product are disclosed, along with methods for inhibiting or reversing fibrotic diseases. Applicants have discovered that key functions of myofibroblasts derived from hypertrophic scars (HTSF) are constitutively activated by an autocrine loop involving Transforming Growth Factor-β1 (TGF-β1). Applicants have also discovered that this autocrine induction of TGF-β1 results in a constitutively high level of Hic-5, which markedly reduces HTSF proliferation in culture relative to normal adult fibroblasts (NADF). Cyclin D1 and A levels are constitutively lower in HTSF compared to NADF and the cyclin dependent kinase inhibitor p21$^{cip1}$ is upregulated in HTSF and located in the nucleus Inhibition of autocrine TGF-β1 production in HTSF reverses this process, lowering Hic-5 and p21$^{cip1}$ levels and increasing replication. Moreover, Hic-5 is partially localized in the nucleus of HTSF, and knocking down Hic-5 with specific siRNAs in these cells results in decreased p21$^{cip1}$ levels and a concomitant increase in proliferation. These unexpected findings demonstrate that autocrine production of TGF-β1 upregulates the expression of Hic-5, which is essential for perpetuating the decreased proliferation seen in pathogenic myofibroblasts. These findings are the first to link the autocrine induction of TGF-β1 with low cell proliferation through the focal adhesion protein, Hic-5, and the data provided herein support a mechanism through which HTSF persist after the wound has healed and serves as a model for other fibrotic disorders.

Applicants have also unexpectedly discovered that Hic-5 is required to maintain, but not initiate, the HTS myofibroblast phenotype. Hic-5 specific siRNAs decrease the generation of supermature focal adhesions, reduce the expression of SMCA, decrease collagen contraction and ECM synthesis, and dramatically reduces TGF-β1 production. These findings demonstrate that Hic-5 is an essential component of the mechanism regulating the autocrine production of TGF-β1 and the pathogenic myofibroblast phenotype. Employing genetic silencing, Applicants have discovered that Hic-5 RNA is reversed the myofibroblast phenotype of HTSF to that of a resting fibroblast phenotype. Applicants also found that Hic-5 was required to maintain the autocrine loop of TGF-β1 in HTSF by regulating TGF-β1 production. Thus, Hic-5 is upregulated by TGF-β1 and, in turn, is required for the production of TGF-β1 in a feed-forward mechanism in which TGF-β1 levels remain constitutively high, thereby maintaining the pathogenic myofibroblast phenotype.

In one aspect, methods for inhibiting or reversing a fibrotic disorder in a mammalian subject are provided herein. In an embodiment, the method includes administering a therapeutically effective amount of a composition containing a Hic-5 antagonist and a pharmaceutically effective carrier.

As used herein the term "fibroproliferative disease" or "fibrotic disease or disorder" refers to conditions involving fibrosis in one or more tissues. As used herein the term "fibrosis" refers to the formation of fibrous tissue as a reparative or reactive process, rather than as a normal constituent of an organ or tissue. Fibrosis is characterized by fibroblast accumulation and collagen deposition in excess of normal deposition in any particular tissue. As used herein the term "fibrosis" is used synonymously with "fibroblast accumulation and collagen deposition". Fibroblasts are connective tissue cells, which are dispersed in connective tissue throughout the body. Fibroblasts secrete a nonrigid extracellular matrix containing type I and/or type III collagen. In response to an injury to a tissue, nearby fibroblasts migrate into the wound, proliferate, and produce large amounts of collagenous extracellular matrix. Collagen is a fibrous protein rich in glycine and proline that is a major component of the extracellular matrix and connective tissue, cartilage, and bone. Collagen molecules are triple-stranded helical structures comprised of three alpha-chains, which are wound around each other in a rope-like helix. Collagen exists in several forms or types; of these, type I, the most common, is found in skin, tendon, and bone; and type III is found in skin, blood vessels, and internal organs.

Fibrotic disorders include, but are not limited to, systemic and local scleroderma, keloids and hypertrophic scars, atherosclerosis, restinosis, pulmonary inflammation and fibrosis, idiopathic pulmonary fibrosis, liver cirrhosis, fibrosis as a result of chronic hepatitis B or C infection, kidney disease, heart disease resulting from scar tissue, and eye diseases such as macular degeneration, and retinal and vitreal retinopathy.

Additional fibrotic diseases include fibrosis resulting from chemotherapeutic drugs, radiation-induced fibrosis, and injuries and burns. Myofibroblasts are also prominent in tumor stroma, providing support for tumor growth and extracellular matrix deposition, and giving rise to characteristics of desmoplastic tumors.

Scleroderma is a fibrotic disorder characterized by a thickening and induration of the skin caused by the overproduction of new collagen by fibroblasts in skin and other organs. Scleroderma may occur as a local or systemic disease. Systemic scleroderma may affect a number of organs. Systemic sclerosis is characterized by formation of hyalinized and thickened collagenous fibrous tissue, with thickening of the skin and adhesion to underlying tissues, especially of the hands and face. The disease may also be characterized by dysphagia due to loss of peristalsis and submucosal fibrosis of the esophagus, dyspnea due to pulmonary fibrosis, myocardial fibrosis, and renal vascular changes. (Stedman's Medical Dictionary, 26.sup.th Edition, Williams & Wilkins, 1995)) Pulmonary fibrosis affects 30 to 70% of scleroderma patients, often resulting in restrictive lung disease (Atamas et al. Cytokine and Growth Factor Rev 14: 537-550 (2003)).

Idiopathic pulmonary fibrosis is a chronic, progressive and usually lethal lung disorder, thought to be a consequence of a chronic inflammatory process (Kelly et al., Curr Pharma Design 9: 3949 (2003)). The causes of this disease are not yet known.

As used herein the term "subject" or "patient" refers to animals including mammals including humans. The term "mammal" further includes primates, domesticated animals including dogs, cats, sheep, cattle, goats, pigs, mice, rats, rabbits, guinea pigs, captive animals such as zoo animals, and wild animals. As used herein the term "tissue" refers to an organ or set of specialized cells such as skin tissue, lung tissue, kidney tissue, and other types of cells.

A "Hic-5 antagonist" according to the present invention inhibits or blocks at least one activity of Hic-5, or alternatively, blocks expression of the focal adhesion protein or other proteins to which it binds ("receptors"). Inhibiting or blocking protein activity can be achieved, for example, by employing one or more inhibitory agents that interfere with the binding of the protein to its receptors, and/or blocks signal transduction resulting from the binding of the protein to its receptors.

In one embodiment, the Hic-5 antagonist comprises a Hic-5 binding agent, which binds to Hic-5 and prevents binding of the protein to its receptors, and/or blocks signal transduction resulting from the binding of the protein to its receptors. These antagonists include, but are not limited to, antagonistic antibodies, peptide or polypeptide binding agents, soluble Hic-5, and small molecule antagonists.

In another embodiment, the antagonist is a Hic-5 antagonist, which binds to this receptor and blocks ligand binding and/or signal transduction. These antagonists include, but are not limited to, antagonistic antibodies, soluble ligands, and small molecules that bind to Hic-5 and interfere with Hic-5 signal transduction and activity.

In another embodiment, the Hic-5 antagonist is a molecule that prevents expression of the Hic-5 protein. These molecules include, for example, antisense oligonucleotides which target mRNA, and interfering messenger RNA. These antagonists prevent or reduce expression of Hic-5 or its receptor. These include antisense or sense oligonucleotides comprising a single-stranded polynucleotide sequence (either RNA or DNA) capable of binding to target mRNA (sense) or DNA (antisense) sequences. Antisense or sense oligonucleotides, according to the invention, comprise fragments of the targeted polynucleotide sequence encoding either Hic-5 or its receptor. Such a fragment generally comprises at least about 14 nucleotides, typically from about 14 to about 30 nucleotides. The ability to derive an antisense or a sense oligonucleotide, based upon a nucleic acid sequence encoding a given protein is described in, for example, Stein and Cohen (Cancer Res. 48:2659, 1988), and van der Krol et al. (BioTechniques 6:958, 1988). Binding of antisense or sense oligonucleotides to target nucleic acid sequences results in the formation of duplexes that block or inhibit protein expression by one of several means, including enhanced degradation of the mRNA by RNAse H, inhibition of splicing, premature termination of transcription or translation, or by other means. The antisense oligonucleotides thus may be used to block expression of proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L)-lysine. Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid by any gene transfer method, including, for example, lipofection, $CaPO_4$-mediated DNA transfection, electroporation, or by using gene transfer vectors such as Epstein-Barr virus or adenovirus.

Sense or antisense oligonucleotides also may be introduced into a cell containing the target nucleic acid by formation of a conjugate with a ligand-binding molecule, as described in WO 91/04753. Suitable ligand binding molecules include, but are not limited to, cell surface receptors, growth factors, other cytokines, or other ligands that bind to cell surface receptors. Preferably, conjugation of the ligand-binding molecule does not substantially interfere with the ability of the ligand-binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid by formation of an oligonucleotide-lipid complex, as described in WO 90/10448. The sense or antisense oligonucleotide-lipid complex is preferably dissociated within the cell by an endogenous lipase.

Additional methods for preventing expression of targeted proteins or protein receptors is RNA interference or RNAi produced by the introduction of specific double-stranded RNA (dsRNA), as described, for example in Bosher et al., Nature Cell Biol 2, E31-E36 (2000). Delivery and inhibition of targeted genes by siRNA in mouse skin models are described in Wang et al., Journal of Investigative Dermatology 2577-2584 (2007).

Figure 11:
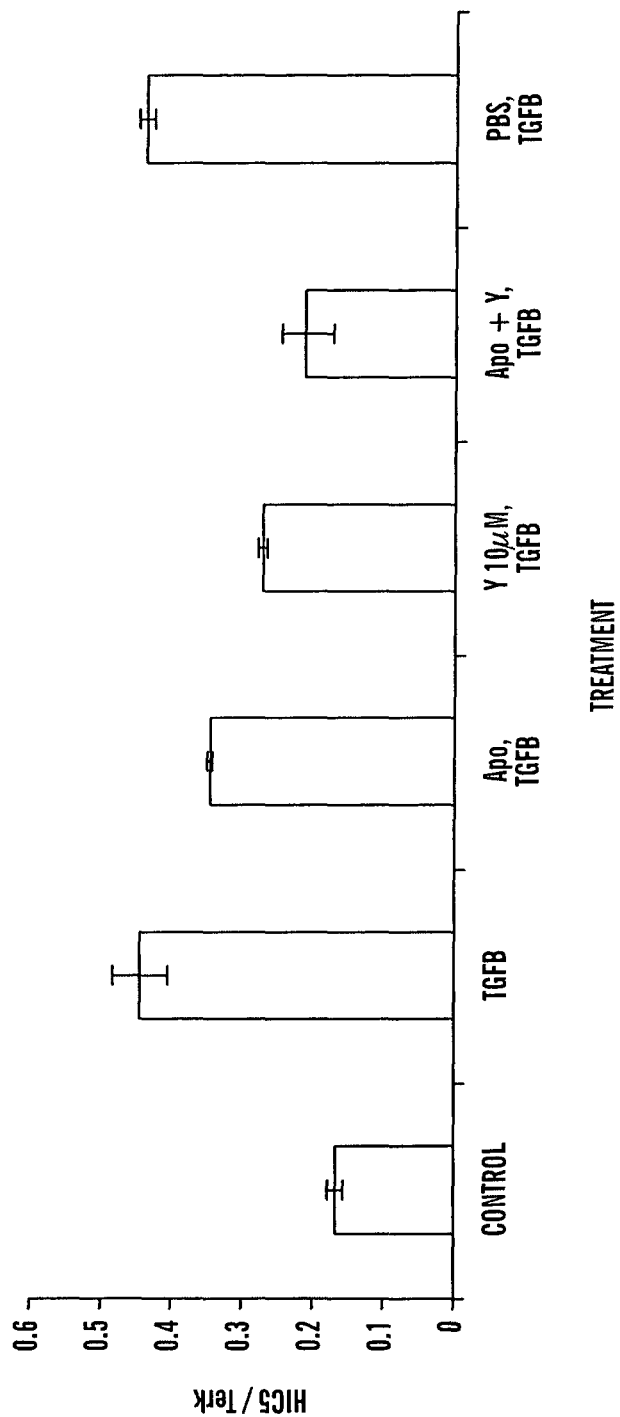
FIG. 11. APO +/or Y-27632 10 μM treatment in HFF cells with TGF-β. Human foreskin, dermal fibroblasts were trypsinized, distributed to wells (32,000 cells per well) in serum-containing Dulbecco's MEM medium overnight. Cells were washed to remove serum-containing medium, shifted to serum-free medium and apocyanin (final concentration 100 micromolar) and Y27632 (10 micromolar) were added. Incubation was continued for 24 hrs in the presence ("TGFB" on figure) or absence ("control") of recombinant, active TGF-beta1. Cells were lysed in sample buffer and analyzed by western blotting with specific antibodies for Hic-5 and a loading control (e.g., total erk). Western blots were then treated with chemiluminescent substrate and expression for Hic-5 and total-erk quantitated. Results are expressed as the levels of Hic-5, normalized to total-erk (a ratio).

In one embodiment, Hic-5 siRNA molecules SEQ ID NO:1 or SEQ ID NO:2 can be used as Hic-5 antagonists to silence expression of Hic-5 thereby inhibiting or reversing a fibrotic disorder in a subject. In another embodiment, Fe-TBAP can be used to inhibit the generation of Hic-5 protein. In still another embodiment, the Rho-kinase inhibitor Y-27632 can be used in combination with apocyanin as a Hic-5 antagonist (FIG. 11).

Fe-TBAP is a known compound and is described in WO 99/023097 for example, which is incorporated herein by reference. Y-27632 and apocyanin are also known compounds and are described in Murata et al. 2003 and Saito et al. 2007, respectively.

In another aspect, the invention provides methods for screening for an agent capable of inhibiting or reversing a fibrotic disorder by providing an animal or cell expressing pathogenic myofibroblasts (or myofibroblastic features), exposing the animal or cell to the agent, and determining the effect of the agent on Hic-5 expression or activity. In an embodiment, the effect of the agent is determined by the change in phenotype, i.e., from pathogenic myofibroblast to normal fibroblast.

Antagonists such as peptides, polypeptides, peptidometics, antibodies, soluble domains, and small molecules are selected by screening for binding to the target protein (i.e., Hic-5) or protein receptor targets, followed by non-specific and specific elution. A number of binding assays are known in the art and include non-competitive and competitive binding assays. Subsequently inhibitory parameters such as $IC_{50}$ (concentration at which 50% of a designated activity is inhibited) and the binding affinity as measured by $K_D$ (dissociation constant) or Ka (association constant) can be determined using cell-based or other assays. $IC_{50}$ can be determined used cell based assays, for example, employing cell cultures expressing cytokine receptors on the cell surface, as well as a cytokine-responsive signaling reporter such as a pLuc-MCS reporter vector (Stratagene cat #219087). The inhibition of signaling when increasing quantities of inhibitor is present in the cell culture along with the cytokine can be used to determine $IC_{50}$. As used herein, the term "specifically binds" refers to a binding affinity of at least $10^6$ $M^{-1}$, in one embodiment, $10^7$ $M^{-1}$ or greater. Equilibrium constant $K_D$ or Ka can be determined by using BIAcore® assay systems such as BIAcore® 3000 (Biacore, Inc., Piscataway, N.J.) using various concentrations of candidate inhibitors according to the manufacturer's suggested protocol. The therapeutic value of the antagonists can then be tested on various animal models such as the tsk1, tsk2, or bleomycin murine models described below in the Example section.

High-throughput screening techniques are also well known to those skilled in the art and can be used to screen for agents capable of inhibiting or reversing fibrosis. The key to HTS is to develop a test, or assay, in which binding between a compound (e.g., a candidate agent) and a protein (e.g., Hic-5) causes some visible change that can be automatically read by a sensor. Typically the change is emission of light by a fluorophore in the reaction mixture. One way to make this occur is to attach the fluorophore to the target protein (e.g., Hic-5) in such a way that its ability to fluoresce is diminished (quenched) when the protein binds to another molecule. A different system measures the difference in a particular property of light (polarization) emitted by bound versus unbound fluorophores. Bound fluorophores are more highly polarized, and this can be detected by sensors.

In another aspect, the invention provides methods for regulating the level of an extracellular matrix (ECM) protein or smooth muscle cell actin (SMCA) produced by a cell by modulating expression or activity of the focal adhesion protein, Hic-5.

In one embodiment, the ECM protein is chosen from collagen, elastin, fibrillin, fibronectin, laminin, and proteoglycan. As used herein, the term "modulating expression or activity of Hic-5" means modifying or altering the expression and/or activity of a Hic-5 protein compared with unmodified levels. Modulating expression may include inducing or increasing the expression and/or activity or reducing the expression and/or activity.

Modulation of Hic-5 expression and/or activity in the cell may be achieved using antagonists, inhibitors, mimetics or derivatives of Hic-5. Modulation of Hic-5 expression and/or activity may be achieved by direct or indirect methods. Modulation of expression and/or activity of Hic-5 may be achieved using direct methods known to those skilled in the art and include, but are not limited to, knockout technology, antisense technology, triple helix technology, targeted mutation, gene therapy, regulation by agents acting on transcription. Indirect methods for modulating expression and/or activity of Hic-5 include but are not limited to targeting upstream or downstream regulators such as cytokines.

In yet another aspect, the invention provides methods of inhibiting the TGF-β1 signaling pathway in a patient in need thereof by administering to the patient a composition comprising a therapeutically effective amount of a Hic-5 antagonist and a pharmaceutically acceptable carrier.

Pharmaceutical compositions containing one or more Hic-5 antagonists according to the present invention are within the scope of the present invention. Such compositions comprise a therapeutically or prophylactically effective amount of each antagonist in admixture with pharmaceutically acceptable materials. As used herein, the term "therapeutically effective amount" or "effective amount" means the total amount of each active component of the pharmaceutical composition or method that is sufficient to show a meaningful patient benefit, e.g., amelioration of symptoms of, healing of, or increase in rate of healing of a fibrotic disorders. When applied to an individual active ingredient, administered alone, the term refers to that ingredient alone. When applied to a combination, the term refers to combined amounts of the active ingredients that result in the therapeutic effect, whether administered in combination, serially or simultaneously. Typically, the antagonists will be sufficiently purified for administration to an animal.

The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants. (Remington's Pharmaceutical Sciences, 18.sup.th Edition, A. R. Gennaro, ed., Mack Publishing Company, 1990).

The optimal pharmaceutical composition will be determined by one skilled in the art depending upon, for example, the intended route of administration, delivery format, and desired dosage. See for example, Remington's Pharmaceutical Sciences, supra. Such compositions may influence the physical state, stability, rate of in vivo release, and rate of in vivo clearance of the therapeutic molecule.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute therefore. In one embodiment of the present invention, antagonist compositions may be prepared for storage by mixing the selected composition having the desired degree of purity with optional formulation agents (Remington's Pharmaceutical Sciences, supra) in the form of a lyophilized cake or an aqueous solution. Further, the therapeutic antagonist may be formulated as a lyophilizate using appropriate excipients such as sucrose.

The pharmaceutical compositions can be selected for the condition to be treated. Treatment of fibrotic disorders may be delivered topically, orally or delivered by injection, for example. Alternatively, the compositions may be delivered, for example, by inhalation therapy, orally, or by injection. The preparation of such pharmaceutically acceptable compositions is within the skill of the art.

The formulation components are present in concentrations that are acceptable to the site of administration. For example, buffers are used to maintain the composition at physiological pH or at slightly lower pH, typically within a pH range of from about 5 to about 8.

When parenteral administration is contemplated, the therapeutic compositions for use in this invention may be in the form of a pyrogen-free, parenterally acceptable aqueous solution comprising the desired antagonist in a pharmaceutically acceptable vehicle. A particularly suitable vehicle for parenteral injection is sterile distilled water in which an antagonist is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In another aspect, pharmaceutical formulations suitable for parenteral administration may be formulated in aqueous solutions, preferably in physiologically compatible buffers such as Hanks' solution, ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions. In another embodiment, a pharmaceutical composition may be formulated for inhalation. For example, an antagonist may be formulated as a dry powder for inhalation. Antagonists including polypeptide or nucleic acid molecule inhalation solutions may also be formulated with a propellant for aerosol delivery. In yet another embodiment, solutions may be nebulized. Pulmonary administration is further described in PCT Application No. PCT/US94/001875, which describes pulmonary delivery of chemically modified proteins, and which is herein incorporated by reference.

It is also contemplated that certain formulations may be administered orally. In one embodiment of the present invention, molecules that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the antagonist molecule. Diluents, flavorings, low melting point waxes, vegetable oils, lubricants, suspending agents, tablet disintegrating agents, and binders may also be employed.

Pharmaceutical compositions for oral administration can also be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally also include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Another pharmaceutical composition may involve an effective quantity of antagonist in a mixture with non-toxic excipients that are suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binders, such as starch, gelatin, or acacia; or lubricating agents such as magnesium stearate, stearic acid, or talc.

Additional pharmaceutical compositions will be evident to those skilled in the art, including formulations involving molecules in sustained- or controlled-delivery formulations. Techniques for formulating a variety of other sustained- or controlled-delivery means, such as liposome carriers, bioerodible microparticles or porous beads and depot injections, are also known to those skilled in the art. See for example, PCT/US93/00829 that describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919, EP 58,481), copolymers of L-glutamic acid and gamma ethyl-L-glutamate (Sidman et al., Biopolymers, 22:547-556 (1983), poly(2-hydroxyethyl-methacrylate) (Langer et al., J. Biomed. Mater. Res., 15:167-277, (1981); Langer et al., Chem. Tech., 12:98-105 (1982)), ethylene vinyl acetate (Langer et al., supra) or poly-D(−)-3-hydroxybutyric acid (EP 133,988). Sustained-release compositions also include liposomes, which can be prepared by any of several methods known in the art. See e.g., Eppstein et al., PNAS (USA), 82:3688 (1985); EP 36,676; EP 88,046; EP 143,949.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present invention is also directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the molecule is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 mg/kg to up to about 100 mg/kg or more, depending on the factors mentioned above. Antibodies may be preferably injected or administered intravenously.

For any compound, the therapeutically effective dose can be estimated initially either in cell culture assays or in animal models such as mice, rats, rabbits, dogs, pigs, or monkeys. An animal model may also be used to determine the appropriate concentration range and route of administration. Such information can then be used to determine useful doses and routes for administration in humans.

The exact dosage will be determined in light of factors related to the subject requiring treatment. Dosage and administration are adjusted to provide sufficient levels of the active compound or to maintain the desired effect. Factors that may be taken into account include the severity of the fibrotic condition, whether the condition is acute or chronic, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

The frequency of dosing will depend upon the pharmacokinetic parameters of the therapeutic antagonist molecule in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data. In addition, the composition may be administered prophylactically.

The route of administration of the pharmaceutical composition is in accord with known methods, e.g. orally, through injection by intravenous, intraperitoneal, intracerebral (intraparenchymal), intracerebroventricular, intramuscular, intraocular, intraarterial, intraportal, intralesional routes, intramedullary, intrathecal, intraventricular, transdermal, subcutaneous, intraperitoneal, intranasal, enteral, topical, sublingual, urethral, vaginal, or rectal means, by sustained release systems or by implantation devices. Where desired, the compositions may be administered by bolus injection or continuously by infusion, or by implantation device.

Alternatively or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

In some cases, an antagonist of the present invention can be delivered by implanting certain cells that have been genetically engineered, using methods such as those described herein, to express and secrete the polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

Pharmaceutical compositions containing the therapeutic antagonists of the present invention are administered to a subject suffering from a fibrotic disorder to inhibit or reverse fibrosis in the subject. Fibrotic disorders include those previously mentioned, e.g., local and systemic scleroderma, interstitial lung disease, idiopathic pulmonary fibrosis, fibrosis arising from chronic hepatitis B or C, radiation-induced fibrosis, and fibrosis arising from wound healing.

The above disclosure describes several preferred embodiments of the invention. The skilled artisan will recognize that other embodiments of this invention, which are not overtly disclosed, may be employed in the practice of this invention. The invention is further illustrated by the following non-limiting examples.

EXAMPLES

Materials and Methods

Cell Culture

All cells used in these studies were cultured (37° C., 5% $CO_2$.) in serum-containing media which consisted of Dulbecco's modification of Eagle's Minimum Essential Medium, 10% fetal bovine serum and 1% penicillin-streptomycin (all of which were obtained from Gibco Invitrogen Corporation, Carlsbad, Calif.). NADF were purchased from Clonetics-Cambrex BioScience (Walkersville, Md.). HTSF were isolated from biopsies taken from hypertrophic scars resected therapeutically from pediatric patients at Shriner's Burn Hospital and Massachusetts General Hospital, (Boston, Mass.). Tissue was processed according to the protocol of Ronnov-Jessen and Peterson (1993) and as described in (Dabiri et al., 2006). All tissues were acquired anonymously under protocols approved by the relevant medical and ethical committees of the Shriner's Burn Center in accordance with the Declaration of Helsinki Principles and patients gave their written, informed consent.

Growth Curve

Cell growth was measured using CyQUANT® Cell Proliferation Assay Kit (C-7026, Invitrogen, Carlsbad, Calif.). In brief, NADF ($1\times10^3$ cells) or HTSF ($1\times10^3$ cells) were plated in duplicate or triplicate in 96 well dishes (Corning Inc., Corning, N.Y.) in complete media with or without the addition of 10 ng/ml of TGF-β1 (R&D Systems, Minneapolis, Minn.) or 20 μg/ml anti-TGF-β (R&D Systems, Minneapolis, Minn.). Plates were incubated for 0, 3, 5, and 7 days, inverted to remove the medium from the wells, and treated according to the manufacturer's protocol. Plates were read on Spectra Max Gemini-EM (Molecular Devices, Sunnyvale, Calif.) with an excitation and emission spectrum 480 nm and 520 nm, respectively.

BrdU Incorporation

HTSF ($5\times10^3$ cells) or NADF ($5\times10^3$ cells) were plated in serum free media (Dulbecco's Minimum Essential Medium 1:1, Hams F12 1:1, transferrin 5 μg/ml, insulin $5\times10^{-7}$M, ascorbate 0.2 mM, glutamine 1:100, penicillin-streptomycin 1:100) for 18 hrs in Labtek™ chambers (Nalge Nunc International, Naperville, Ill.) at 37° C. Cells were washed three times with Dulbecco's phosphate buffered saline (DPBS) (Gibco Invitrogen International, Carlsbad, Calif.) and to each well DMEM containing serum was added, 10 μg/ml of BrdU (Biodesign International, Saco, Me.), with or without the addition of 10 ng/ml of TGFβ1. In some wells anti-TGF-β (20 μg/ml) was also added as indicated. Cells were incubated (24 hrs), washed with DPBS, fixed with 3.7% formaldehyde (Sigma Chemical Co., St. Louis, Mo.) in DPBS (10 min), permeabilized with 0.5% Triton X-100 (5 min) (Sigma Chemical Co., St. Louis, Mo.), blocked (1 hr) with 2% bovine serum albumin (Sigma Chemical Co., St. Louis, Mo.) in PBS then DNAase (Promega, Madison, Wis.) treated for 30 min. All primary and secondary antibodies were diluted in 2% BSA (Sigma Chemical Co., St. Louis, Mo.) in PBS. Samples were then incubated sequentially with mAb against BrdU (10 μg/ml in 2% BSA/PBS) and then with a mixture of donkey anti-sheep Alexa Fluor 488 (1:200, in 2% BSA/PBS) and Hoechst 33342 (1:1000) (both from Molecular Probes, Sunnyvale, Calif.). Coverslips were mounted in Gelmount (Biomedia Corp., Biomedia Corp., Foster City, Calif.) and slides were analyzed on an Olympus BX60 microscope using 10× objective. Images were captured with attached Cooke Sensicam digital camera and deconvolved using Slidebook 3.0.10.3 software (FFTW licensed from Massachusetts Institute of Technology, Cambridge, Mass.). The percent positive BrdU incorporation was determined by dividing the number of nuclei labeled with both BrdU (green) and Hoescht (blue) by the total number of nuclei (blue)×100.

Luciferase MLEC Assay

Mink Lung Epithelial cells (MLECs-clone 32) were stably transfected with an 800 bp fragment (−799−>+71) of the 5' end of the human plasminogen activator inhibitor-1 (PAI-1) gene promoter engineered to drive the firefly luciferase reporter gene in a p19LUC-based vector containing the neomycin-resistance gene from pMAMneo (Abe et al., 1994). Transfected MLECs were maintained in DMEM supplemented with 10% fetal bovine serum, penicillin (100 U/ml), streptomycin (100 μg/ml), L-glutamine, and G418 (Geneticin, 200 μg/ml). In some experiments, MLEC ($5\times10^3$ cells) were plated either with or without the addition of anti-TGF-β (10 ng/ml) and/or active TGF-β1 (5 ng/ml) to test the efficiency of blocking conditions. In other experiments, MLEC were co-cultured (37° C., 5% $CO_2$, 24 hr) with NADF ($5\times10^3$ cells) or HTSF ($5\times10^3$ cells) in serum-containing media (as described above) with or without the addition of anti-TGF-β (20 μg/ml). Luciferase activity was measured by addition of Bright-Glo™ Luciferase Assay System (Promega, Madison, Wis.) to cells (5 min) and quantitated on Monolight™ 3010 reader (Pharmingen, Franklin Lakes, N.J.).

Western Blot

NADF and HTSF lysates were analyzed for protein expression by western blotting with the following primary antibodies at a concentration of 1:1000: cyclin D1, (BD-Biosciences; DCS-6, San Jose, Calif.), cyclin A, (Santa Cruz Biotech.; H 432, Santa Cruz, Calif.), $p21^{cip1}$ (BD-Biosciences; sx-118, San Jose, Calif.), $p15^{ink4b}$ (Cell Signaling, Danvers, Mass.), Hic-5 (BD Transduction, Franklin Lakes, N.J.), RhoGDI (Santa Cruz Biotech, Santa Cruz, Calif.), H2A (Cell Signaling, Danvers, Mass.) and ERK½ (Santa Cruz Biotech, Santa Cruz, Calif.), Vinculin (Sigma Aldrich), SMCA (Sigma Aldrich), FN (Neomarkers), Collagen type I (Sigma Aldrich), Paxillin (Sigma Aldrich). Western blots were developed using SuperSignal chemiluminescent substrate (Pierce, Rockford, Ill.) and quantitated with a Fluor-S MultiImager and Quantity-One software (Bio-Rad, Hercules, Calif.). Membranes were stripped using Restore Stripping (Pierce, Rockford, Ill.) and reprobed (no more than once) with other antibodies.

Subcellular Fractionation

Either NADF ($5\times10^3$ cells) or HTSF ($5\times10^3$ cells) were cultured in DMEM plus serum for 24 hrs with either TGF-$\beta$1 (10 ng/ml) or anti-TGF-$\beta$1 (20 µg/ml) where indicated. Cells were washed with ice cold PBS twice on ice, lysed in BN buffer (1 ml) (15 mM tris, pH 7.5, 60 mM KCl, 5 mM $MgCl_2$, 156 nM NaCl, 250 nM sucrose) containing 0.15% NP40 (Sigma Chemical Co., St. Louis, Mo.) on ice. Cells were then pelleted (500 g for 4 min, 4° C.) and the cytosolic fraction (supernatant) was removed. The nuclear fraction (pellet) was resuspended in BN buffer (1 ml) without NP40, spun at 500 g for 4 min at 4° C., and the supernatant was discarded. To the pellet (nuclear fraction) 100 µl of 1× sample buffer with DTT was added. To 25 µl of cytosol fraction, 75 µl of 4× sample buffer with DTT was added. Protein expression was analyzed by western blot, as described above.

RNA Interference (RNAi)

Human Hic-5 is located on chromosome 16 at location 16p11.2 and its NCBI Accession No. is NM_015927 (mRNA). NADF or HTSF were transfected with short interference RNA (siRNA) (Dharmacon, Lafayette, Colo.) using OligofectAMINE (Invitrogen, Carlsbad, Calif.). Hic-5 knockdown was performed using individual siRNA sequences: duplex #1 (GGAGCUGGAUAGACUGAUGUU) (SEQ ID NO:1) and duplex #2 (GGACCAGUCUGAA-GAUAAGUU) (SEQ ID NO:2). Cells were transfected for 4 hrs in OptiMem (Gibco Invitrogen Corporation, Carlsbad, Calif.) and re-fed with DMEM with serum. Cells were trypsinized after 5 days and replated for experiments.

Adenovirus Production

Full-length mouse Hic-5 cDNA (kindly provided by Dr. Sheila Thomas, Harvard Medical School, Boston, Mass.) was subcloned into pEGFPc1 (BD Clontech). Adenovirus was produced utilizing the Adeno-X system according to the manufacturer's instructions (BD Clontech, Mountain View, Calif.). Briefly, the GFP-Hic-5 was excised from the pEGFPc1 vector and subcloned into the pShuttle vector. Restriction digest of the pShuttle construct with the unique endonucleases I-Ceu I and PI-Sce I was performed followed by subcloning into the adenovirus vector. Adenoviral stocks were amplified in Ad-HEK cells (Stratagene, La Jolla, Calif.) and titered by limited dilution assay in 96-well plates. The GFP adenovirus was kindly provided by Dr. A. Hassid (University of Tennessee, Memphis, Tenn.). 50,000 cells were plated in serum-containing media for 24 hrs. Next day cells were washed twice with serum-free media, then serum-free media was added and cells were infected with an MOI of 100 pfu/cell. Experiments were performed 24 hrs following infection.

RT-PCR

Total RNA was extracted from cells using the PURE-SCRIPT RNA Isolation kit (Gentra Systems, Minneapolis, Minn., USA). RNA (1/10th) was reverse transcribed and 1 µg of the resulting complementary DNA (cDNA) was utilized to detect mRNA abundance with primers for TGF-$\beta$ (forward: 5'-GTACCTGAACCCGTGTTGCT (SEQ ID NO:3); reverse: 5'-GAACCCGTTGATGTCCACTT (SEQ ID NO:4)), Hic-5 (Forward 5'-GCTAGATCGGTTGCTTCAGG (SEQ ID NO:5); reverse 5'-GCGGAAGTCAGAGAGT-GAGG (SEQ ID NO:6)) and GAPDH as control, (forward: 5'-CATGGCCTCCAAGGAGTAAG (SEQ ID NO:7); reverse: 5'-GGTTGGCACAGGGTACTTTA (SEQ ID NO:8)). All primers were designed to give ~200-350 base pair products. PCR reactions were carried out as previously described (Dabiri et al., in press).

Floating Collagen Lattice

Before preparing the gels, 5 ml of BSA (Sigma) solution (0.1% BSA in PBS, filter sterilized) was pipetted into each well of a six-well plate, incubated at 37° C. for 1 hour. 1.4 ml of bovine dermal collagen Vitrogen (Cohesion, Palo Alto, Calif.) was mixed with 0.4 ml of 5×DMEM in a 15 ml centrifuge tube cooled on ice. The pH was adjusted to a range of 7.2-7.5, using a sterile solution of 1N NaOH. The control and modified cells were trypsinized from a confluent tissue culture plate and 0.2 ml of the cell suspension (containing $5\times10^5$ cells) was added to the collagen solution, gently mixed and poured into a well of the six-well plate. Collagen lattices were allowed to gel for 60 minutes in a 5% $CO_2$ atmosphere at 37° C. After 60 minutes, the collagen lattices were detached from the surface of the well by rimming the lattice with a sterile spatula and gently swirling the six-well plate. 2 ml of serum-free medium was added to each well. Plates were incubated in a 5% $CO_2$ atmosphere at 37° C. To measure contraction, the tissue culture dishes were periodically placed on top of a transparent metric ruler on an opaque background, and the diameters of the lattices were recorded.

Immunofluorescence

Cells were stained as previously described (Dabiri et al., 2006), with slight modification. Control or modified cells were cultured at 30% confluency in complete medium for 18 hours, then washed with Dulbecco's phosphate-buffered saline and serum-free medium was added, followed by 10 ng/ml of TGF-$\beta$1 or 20 ng/ml of anti-TGF-$\beta$1 (R&D Systems, Minneapolis, Minn.) where specified. Cells were allowed to incubate for 5 days. On the fifth day, cells were washed fixed, permeabilized, and blocked for 1 hour. Samples were then incubated sequentially with mAb against vinculin (1:400) (Sigma Chemical Co., St Louis, Mo.), and then with a mixture of goat anti-mouse Alexa Fluor 488 (1:1000) and TRITC-conjugated phalloidin (1:100). Coverslips were mounted, labeled cells were observed with an Olympus BX60 microscope equipped with an immersion oil objective (×100/1.25, phase 3 or ×100/1.25, phase 3). Images were captured with attached Cooke Sensicam digital camera and deconvolved using Slidebook 3.0.10.3 software (FFTW licensed from Massachusetts Institute of Technology, Cambridge, Mass.).

Focal Adhesion Measurements

Focal adhesion measurements were performed as described previously (Dabiri et al., 2006). In brief, cells (n=20) were chosen that were not in contact with any other cell and were well spread. Images were observed using Olympus BX60 microscope equipped with an immersion oil objective (×60/1.25, phase) and captured as described above. Vinculin staining was measured for area ($\mu m^2$) of focal adhesion using Image Pro-Plus version 4.5.1.26 (Media Cybermatic, Silver Spring, Md.). The limits set for measurement was 1-50 $\mu m^2$ (6.34 pixels/nm).

Measurement of TGF-$\beta$1 Levels by ELISA

Conditioned serum-free media from control and modified fibroblasts were collected at the end of five days and levels of TGF-$\beta$1 were measured by ELISA (R&D Systems, Minneapolis, Minn.). The antibodies used in the ELISA kit are only able to detect TGF-$\beta$1 in its active form, thus samples were activated by acidification (HCl) before ELISA to determine the amount of latent-TGF-$\beta$1 in the condition media (Total measured TGF-$\beta$1 minus active TGF-$\beta$1 levels). After collecting the condition media, cells were treated with trypsin, counted, and the values of TGF-$\beta$1 were normalized by the volume of medium in the dish divided by the final cell number.

Statistics

Statistical comparisons between sample groups were made using an analysis of variance with $p \leq 0.005$ indicating a significant difference between the groups.

Example 1

Autocrine Induction of TGF-β1 Slows Proliferation in Pathogenic Myofibroblasts Through a Mechanism Requiring the Focal Adhesion Protein, Hic-5

Autocrine Induction of TGF-β1 Decreases the Proliferation of HTSF.

It has been previously established that HTSF produce and activate much higher levels of TGF-β1 than do NADF and that this autocrine TGF-β1 loop results in the stable generation of "supermature" focal adhesions (Dabiri et al., 2006). During the course of these studies, it was observed that HTSF grew slowly in culture and sought to determine whether autocrine TGF-β1 production regulated HTSF proliferation. HTSF or NADF were co-cultured with MLEC expressing the PAI-1 luciferase construct, with or without the addition of anti-TGF-β (antibody to block TGF-β1 actions) (20 µg/ml). The PAI-1 promoter is regulated by TGF-β1 and the MLEC-PAI-1 luciferase system is commonly used to evaluate TGF-β1 mediated transcriptional activity (Abe et al., 1994). Using this assay, it was observed that HTSF produce and activate TGF-β to a greater extent (as determined by the luciferase activity) compared to NADF (FIG. 1a). The addition of anti-TGF-β to NADF and HTSF reduced the TGF-β response of the PAI-1 promoter (FIG. 1a). To ensure that the blocking conditions were specific and saturating, the MLEC-PAI-1 reporter expressing cells were cultured alone and tested for the ability of anti-TGF-β to block the response generated by recombinant, active TGF-β1. It was discovered that 10 ng/ml of anti-TGF-β was able to block the response of 5 ng/ml of active TGF-β1 (FIG. 1b).

Since active TGF-β1 has been shown to have inhibitory effects in fibroblast proliferation it was next determined whether autocrine induction of TGF-β1 dampened HTSF proliferation and/or entry into S-phase. Growth curves were conducted by culturing equal cell numbers (see materials and methods section) of either HTSF or NADF, in the presence or absence of active TGF-β1 (10 ng/ml) (FIG. 1c). To test the dependence of HTSF proliferation on the autocrine production of TGF-β1, an antibody to TGF-β (anti-TGF-β) was added to some cultures. Cell numbers were determined at 0, 3, 5, and 7 days after culturing, and it was found that HTSF proliferated slower compared to NADF, (expressed here as the increase in cell number by day 3; cell number at day 3 minus the cell number at day 0). Time points taken at day 5 and day 7 yielded the same relative increase between day 0 and day 3. Addition of 10 ng/ml of TGF-β1 to NADF resulted in a statistically significant decrease in proliferation to levels close to that of HTSF (FIG. 1c). In cultures of HTSF, inhibition of autocrine produced TGF-β with an antibody to active TGF-β resulted in a statistically significant increase in the growth potential of HTSF to levels observed with NADF in the absence of TGF-β1 (FIG. 1c). Anti-TGF-β did not appreciably alter the growth of NADF, indicating that the proliferation of these cells is not regulated by the autocrine production of TGF-β.

To test HTSF and NADF for altered entry into S phase, cells were serum-starved over night. The next day cells were pulsed with BrdU for 24 hours and cultured in serum-containing medium and the percentage of cells incorporating this tracer into DNA was determined. NADF without the addition of TGF-β1 (10 ng/ml) (FIG. 1d, I) after 24 hours had significantly more BrdU-positive nuclei compared to HTSF (FIG. 1d, IV). Addition of 10 ng/ml of TGF-β1 to cultures of NADF (FIG. 1d,II) resulted in a statistically significant decrease in the percent positive nuclei to levels observed in HTSF (FIG. 1d, IV). Inhibition of the autocrine induction of TGF-β1 in HTSF with exogenous anti-TGF-β (FIG. 1d, VI) resulted in a significant increase in BrdU positive nuclei. These data suggest that the autocrine induction of TGF-β1 blocks entry into S-phase, thereby decreasing HTSF proliferation.

TGF-β1 Controls the Expression of Major Cell Cycle Regulatory Molecules.

Figure 2A:
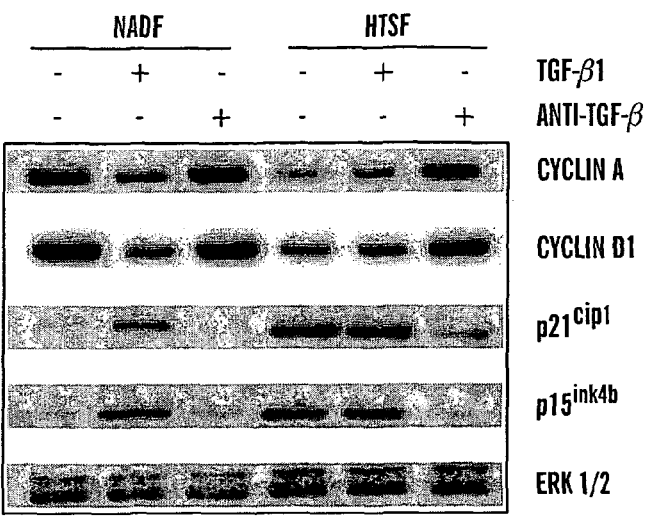
FIGS. 2(A)-(F): G1/S cell cycle proteins are regulated by TGF-β1. Cells were incubated in serum-containing media for 24 hours with or without the addition of either TGF-β1 (10 ng/ml) or anti-TGF-β (20 µg/ml). (2A) Cells were then lysed and directly resolved by SDS-PAGE (10% or 15%) and analyzed by western blot; (2B) and (2C) represent the fold difference for cyclin A and p21 respectively. (2D) Cells were fractionated into nuclear and cytoplasmic (cytosolic) fractions then resolved by SDS-PAGE (15%) gels, transferred to nitrocellulose membrane and analyzed for the designated protein by western blotting. Blots included markers for cytosolic (RhoGDI) and nuclear (H2A) fraction and for protein loading (Erk 1/2). *$p<0.005$, n=3. (2E) and (2F) represent the fold difference for the nuclear fraction and cytosolic fraction, respectively.

Because slower HTSF proliferation and decreased BrdU incorporation compared to NADF was observed, it was next determined whether TGF-β1 altered the levels of G1 cell cycle proteins. Cell lysates were obtained from either NADF or HTSF cultured in serum containing media for 24 hours, either with or without the addition of TGF-β1 (10 ng/ml) or anti-TGF-β (20 µg/ml). The levels of cyclin A and cyclin D1 were approximately 3-fold higher in NADF compared to HTSF, (FIG. 2a). The addition of TGF-β1 to NADF resulted in decreased cyclin A and cyclin D1 levels, similar to those of HTSF control. Inhibition of the autocrine loop of TGF-β1 (anti-TGF-β) resulted in approximately a 5-fold and a 4-fold increase in cyclin A and cyclin D1 levels in HTSF, respectively, compared to HTSF control. The fold differences for cyclin A and $p21^{cip1}$ between NADF and HTSF are graphically represented.

Regulation of cell cycle progression occurs, in part, through a balance in the cyclins and their inhibitors (Ravitz and Wenner 1997). Therefore, the endogenous levels of each of the proteins was examined. Since it has been previously shown that TGF-β1 regulates the expression of several cyclin dependent kinase inhibitor (CDKI) proteins in the cip/kip and ink4 families (Ravitz and Wenner 1997), the effect of TGF-β1 on these inhibitors in control and pathogenic fibroblasts was determined. It was found that $p21^{cip1}$ and $p15^{ink4b}$ were expressed at significantly lower levels in NADF compared to HTSF (2-fold and 6-fold respectively). Addition of TGF-β1 to NADF resulted in a statistically significant increase in the levels of $p21^{cip1}$ and $p15^{ink4b}$ compared to NADF without TGF-β1 (2.5-fold and 5.25-fold increase, respectively). Inhibition of TGF-β1 with a specific antibody in HTSF resulted in a statistically significant decrease in the expression of $p21^{cip1}$ and $p15^{ink4b}$ compared to HTSF-TGF-β1 (2-fold and 14-fold, respectively). These results indicated that TGF-β1 controls the expression of cell cycle proteins; cyclin D1, cyclin A, $p21^{cip1}$, and $p15^{ink4b}$ and together point to a critical role for autocrine TGF-β1 in regulating cell growth in HTSF (FIG. 2a). The endogenous expression and TGF-β1 control over $p27^{kip1}$ was also analyzed. It was found that $p27^{kip1}$ is upregulated in HTSF compared to NADF, however, its expression was not controlled by TGF-β1.

Figure 1E:
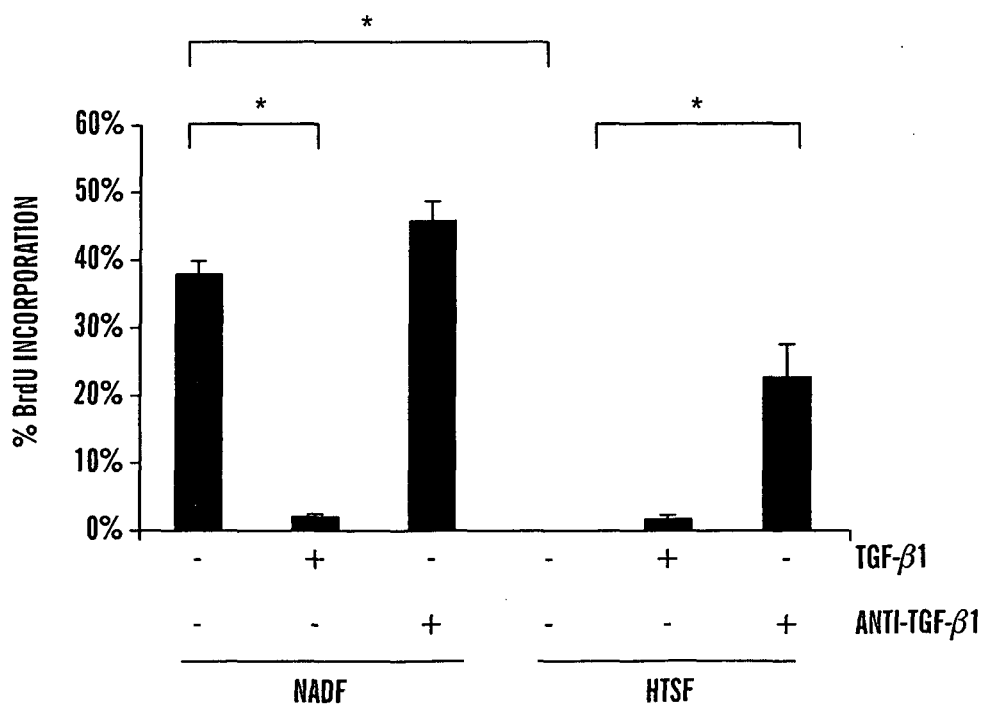
Figure 2B:
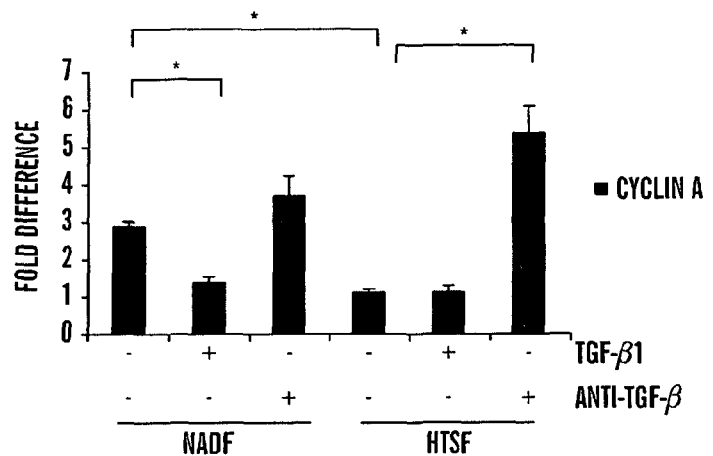
Figure 2C:
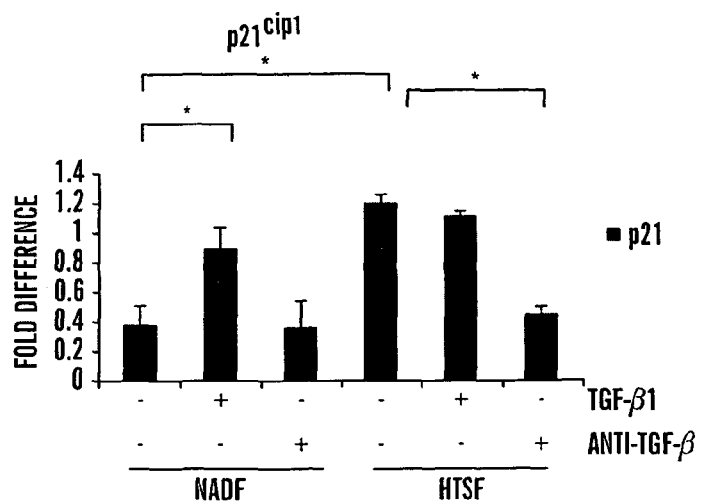
Figure 2D:
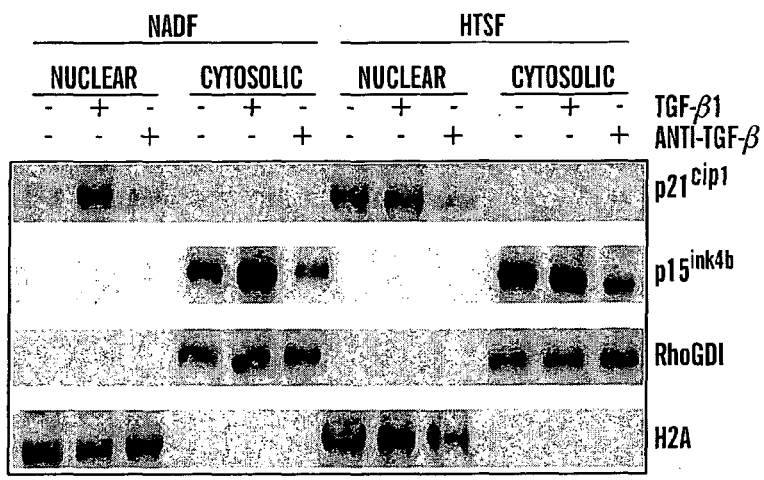
Figure 2E:
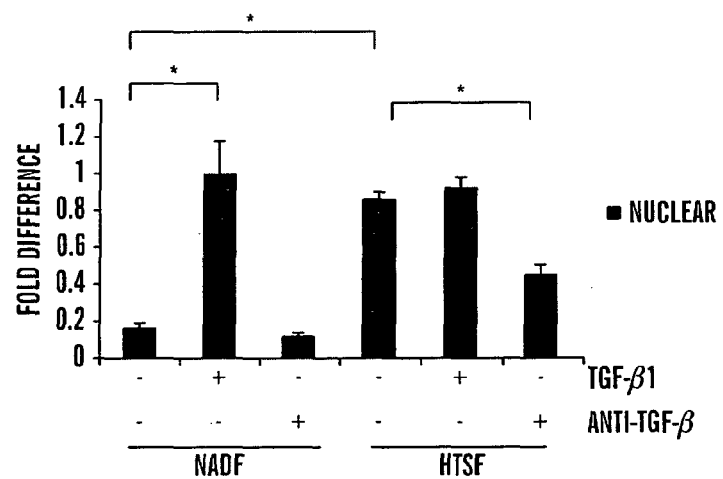
Figure 2F:
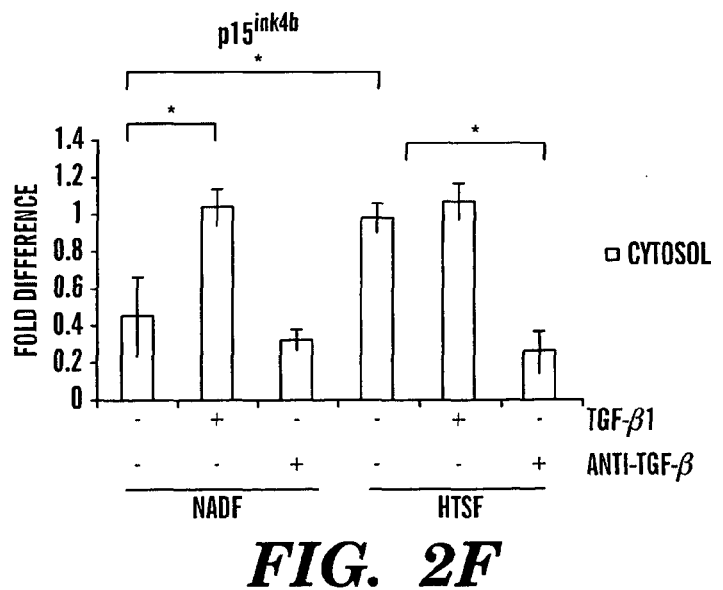

The subcellular localization of the cyclin kinase inhibitors $p15^{ink4b}$ and $p21^{cip1}$ was also determined since the majority of cell cycle control occurs in the nucleus (FIG. 2b). Upon subcellular fraction, it was found that $p15^{ink4b}$ is predominantly localized in the cytosol of both NADF and HTSF but its expression is upregulated in HTSF compared to NADF (2.5-fold). However, $p21^{cip1}$ was predominately localized in the nucleus in both HTSF and NADF, but at a 5-fold higher expression level in HTSF compared to NADF. These results indicate that $p21^{cip1}$ is the major cyclin kinase inhibitor controlled by TGF-β1 resulting in the decreased proliferation seen in HTSF. Consistent with the absence of an appreciable TGF-β autocrine loop in NADF, no significant differences in either the growth rate (FIG. 1c), BrdU incorporation rate (FIG. 1d), or levels of cell cycle proteins with the addition of an antagonist to active TGF-β were observed (FIG. 2a). Conversely, since HTSF secrete and activate their own TGF-β1, the addition of exogenous TGF-β1 did not significantly alter the growth, BrdU incorporation, or cell cycle proteins compared to HTSF without exogenous TGF-β1; while addition of anti-TGF-β to HTSF did reverse the slow rate of proliferation (FIGS. 1 and 2).

Hic-5 Expression is Regulated by the Autocrine Induction of TGF-β1 and Controls Key Molecules Necessary for Cell Cycle Progression in HTSF.

Figure 3A:
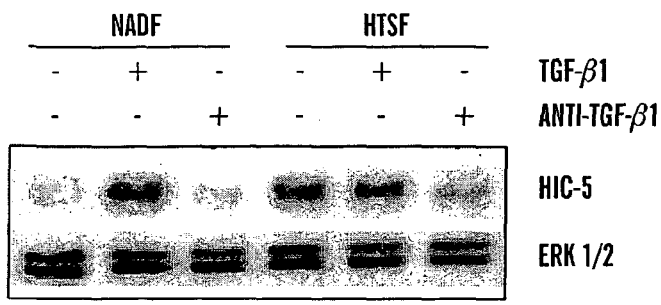
FIGS. 3(A)-(C): Hic-5 expression is regulated by TGF-β1 and localized to the nucleus in HTSF. Cells were incubated in serum-containing media for 24 hours with or without the addition of either TGF-β1 (10 ng/ml) or anti-TGF-β (20 µg/ml). (3A, 3B) Cells were then lysed and directly resolved by SDS-PAGE (10%) and analyzed by western blot. (3C) Cells were fractionated into nuclear and cytoplasmic (cytosolic) fraction as previously described, and the expression of nuclear Hic-5 is shown (3C) as the fold difference compared to HTSF without TGF-β1. *$p<0.005$, n=3.

As shown above, HTSF elaborate an autocrine loop of TGF-β1, which resulted in the upregulation of $p21^{cip1}$ and a slower cellular replication compared to NADF (FIGS. 1 and 2). The expression level of Hic-5 in HTSF was next examined, since Hic-5 is a TGFβ1 inducible protein, and Hic-5 can activate the p21 promoter when localized to the nucleus (Shibanuma et al., 2004). NADF and HTSF were cultured in serum containing media for 24 hours with or without the addition of either TGF-β1 (10 ng/ml) or anti-TGF-β (20 µg/ml). The cells were then lysed and analyzed for the expression of Hic-5 (FIG. 3a). HTSF constitutively expressed Hic-5 at a 2.5-fold higher level compared to NADF in the absence of exogenous TGF-β1 (FIG. 3a). The addition of TGF-β1 to NADF significantly increased the expression of Hic-5 to levels similar to HTSF Inhibition of TGF-β1 by anti-TGF-β resulted in a statistically significant decrease in the endogenous expression of Hic-5 in HTSF (2.5-fold). These results demonstrated that Hic-5 is regulated by TGF-β1 in NADF and that the autocrine induction of TGF-β1 in HTSF resulted in constitutively high levels of endogenous Hic-5.

Figure 3B:
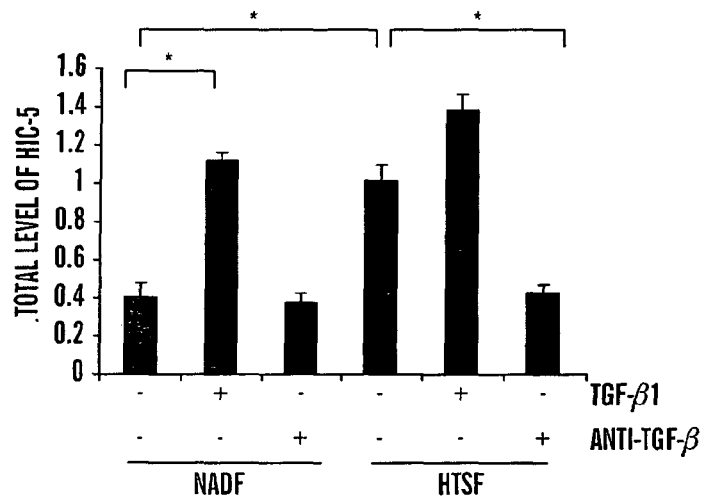
Figure 3C:
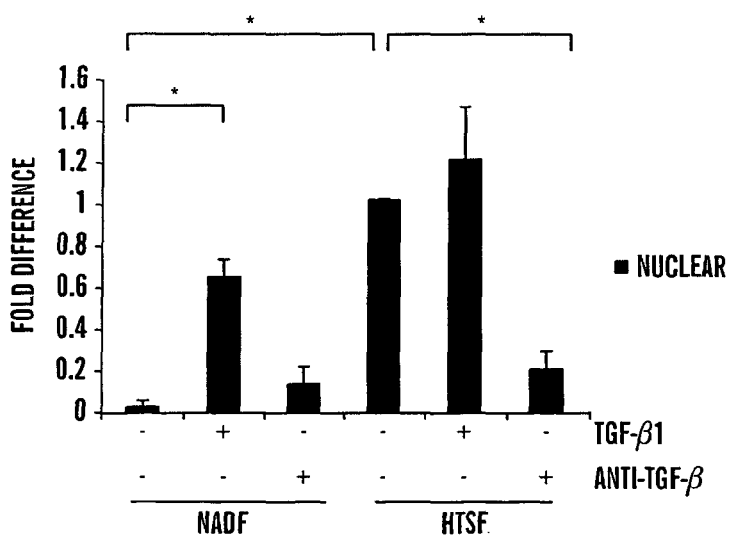

Since nuclear Hic-5 can regulate $p21^{cip1}$ transcriptionally (Shibanuma et al., 2004) and cytosolic Hic-5 can localize to the focal adhesions (Thomas et al., 1999), the localization of Hic-5 in NADF and HTSF was next determined. Upon subcellular fractionation of NADF and HTSF (FIG. 3b), minimal levels of Hic-5 in the nucleus of NADF without the addition of TGF-β1 compared to HTSF were observed (FIG. 3b). The addition of TGF-β1 significantly increased the expression of Hic-5 in the nucleus in NADF. Conversely, inhibition of TGF-β with anti-TGF-β (20 µg/ml) significantly decreased the expression of Hic-5 in the nucleus in HTSF (FIG. 3b).

Figure 4A:
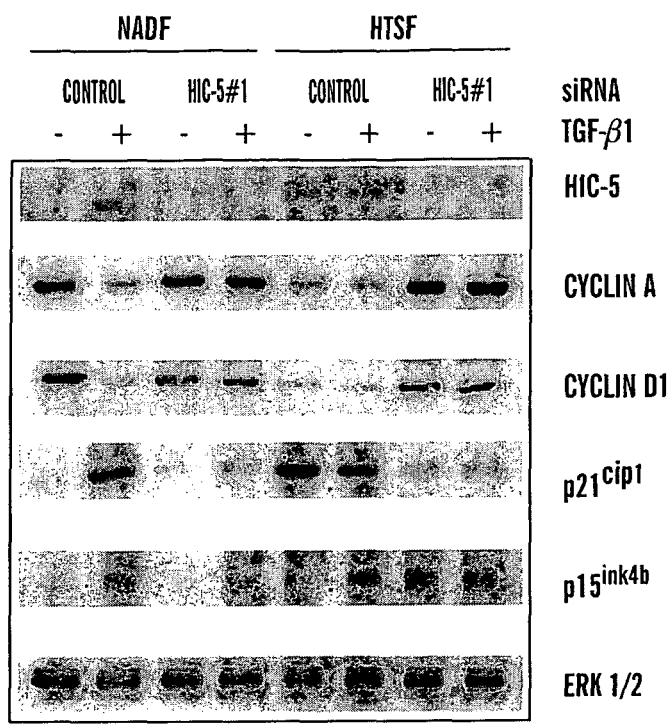
FIGS. 4(A)-(F): Hic-5 controls the expression of cell cycle molecules. (4A) Cells were transfected for 5 days with two separate siRNA Hic-5 duplexes (duplex #2, data not shown), or scrambled control. After transfection, cells were lysed and protein expression analyzed by western blot as in FIGS. 2 and 3. Blots were probed for the indicated proteins; results are represented as fold difference for (4C) cyclin A and (4D) p21. (4B) siRNA Hic-5 transfected cells were infected with either an adenoviral GFP-full length Hic-5 or control GFP construct. Adenoviral transduction resulted in >90% infected cells by fluorescence microscopy for GFP (data not shown). Cells were then lysed and lysates were resolved by SDS-PAGE (10% or 15%) and transferred to nitrocellulose as described previously. Blots were probed for the indicated proteins; results are represented as fold difference for (4E) cyclin A, and (4F) p21. *$p<0.005$, n=5.

Since the levels of Hic-5 were upregulated and Hic-5 is present in the nucleus of HTSF, it was determined whether inhibition of Hic-5 in HTSF controlled the expression of cell cycle proteins. Either Hic-5 or control siRNAs were transfected into either HTSF or NADF for 5 days. After the fifth day, cells were trypsinized and cultured in the presence or absence of TGF-β1 (10 ng/ml); after 24 hrs cells were lysed and protein expression levels analyzed (FIG. 4a). Initially, a pool of four siRNA was used, the pool was deconvolved and two specific siRNAs to Hic-5 were employed. Both with the pooled and the individual siRNAs (duplex #2) resulted in a greater than 90% decrease in the expression of Hic-5 in both NADF and HTSF under basal conditions (FIG. 4a). Hic-5 knockdowns also efficiently blocked TGF-β1 mediated increases in Hic-5 expression (FIG. 4a). The effect of Hic-5 knockdown on $p21^{cip1}$ levels was determined next. siRNA to Hic-5 resulted in a 5-fold decrease in the expression of $p21^{cip1}$ in HTSF and the addition of exogenous TGF-β1 did not significantly restore the expression of $p21^{cip1}$ in both NADF and HTSF. The addition of TGF-β1 increased the expression $p15^{ink4b}$ in NADF by 4-fold; however, this up-regulation was unaffected by knockdown of Hic-5 (FIG. 4a). Inhibiting the expression of Hic-5 in HTSF increased the expression of cyclin A and cyclin D1. In the absence of Hic-5, the addition of exogenous TGF-β1 did not decrease the expression of both cyclin A and cyclin D1 in NADF (FIG. 4a). These data demonstrate that Hic-5 is a necessary intermediate in TGF-β-dependent growth modulation of HTSF and NADF.

Figure 4B:
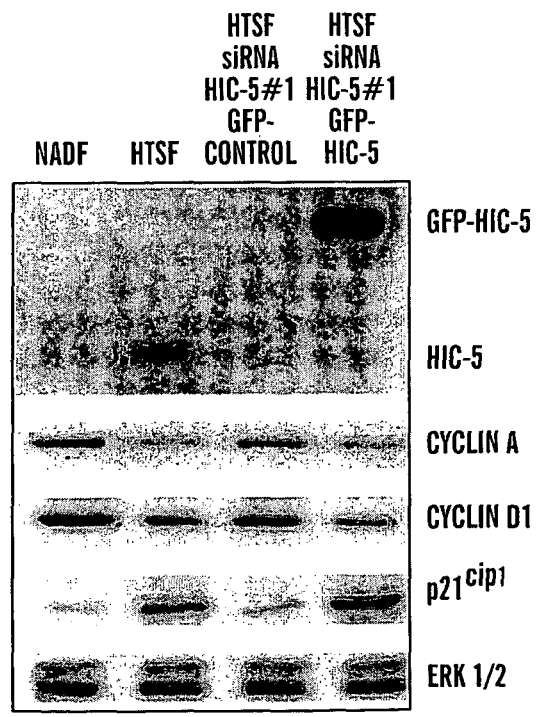
Figure 4C:
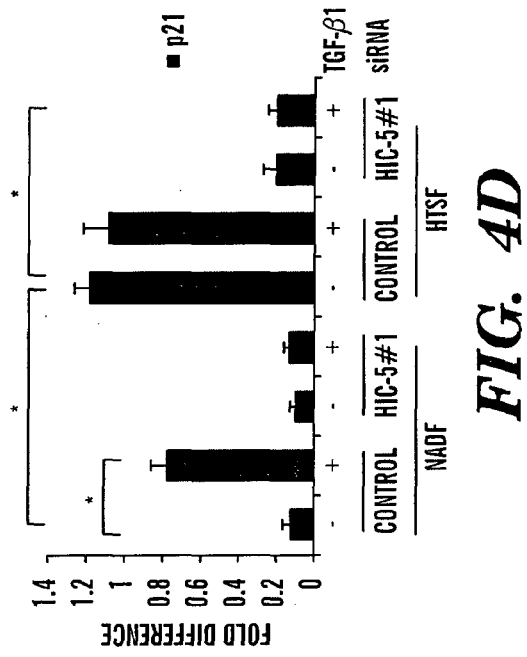
Figure 4D:
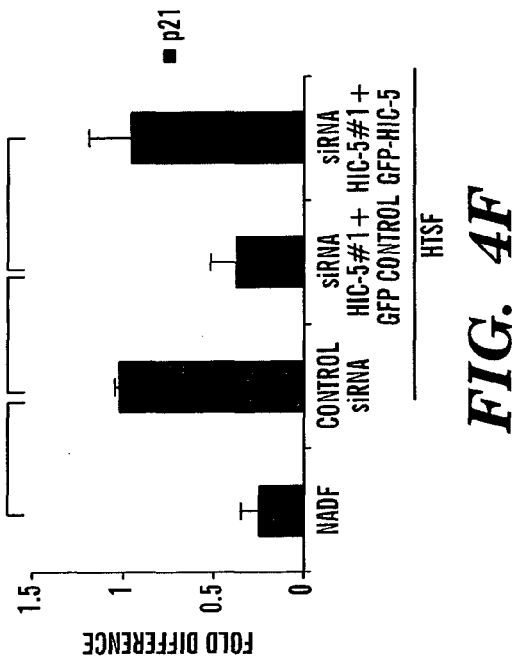
Figure 4E:
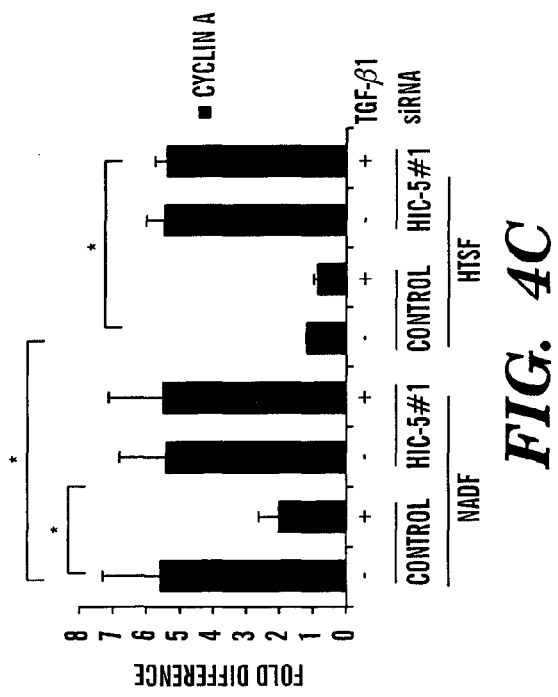
Figure 4F:
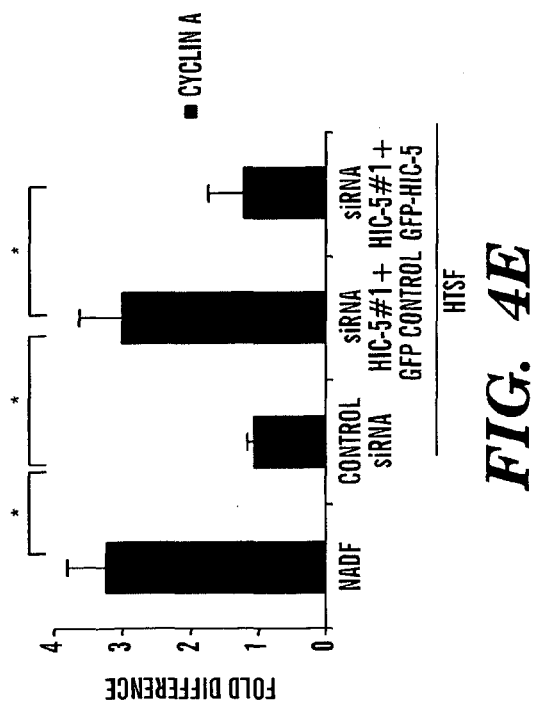

To establish the specificity of the Hic-5 siRNA knockdown in HTSF, experiments to rescue the expression of Hic-5 using an adenoviral GFP-construct were performed. Efficient transduction (>90%) of cells by fluorescence microscopy was observed. Upon rescue of Hic-5 siRNA transfected cells with the Hic-5 adenovirus in HTSF, $p21^{cip1}$ levels were restored and the expression of cyclin D1 and cyclin A were once again decreased (FIG. 4b). Adenoviral rescue of Hic-5 siRNA duplex #2 yielded the same results as duplex #1. These data demonstrate that Hic-5 is strictly necessary as a downstream signaling target of TGF-β1-mediated control over proliferation in HTSF.

Hic-5 Overexpression is Sufficient to Control Molecules Necessary for Cell Cycle Progression in NADF.

Figure 5A:
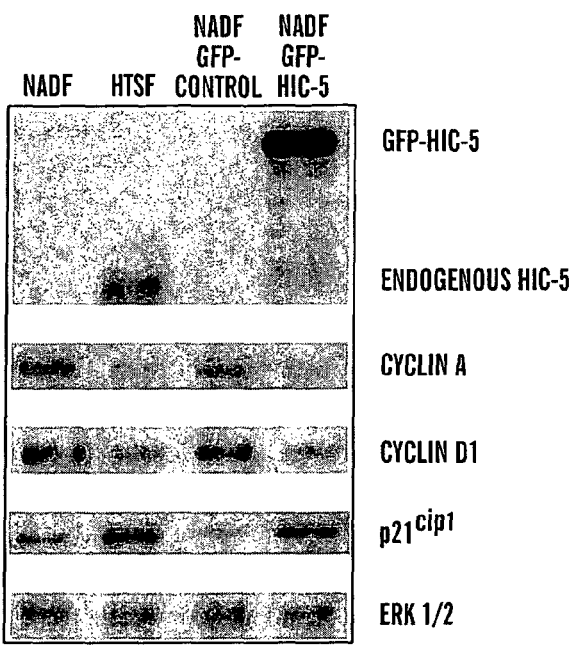
FIGS. 5(A)-(5C): Overexpressing Hic-5 regulates the expression of cell cycle proteins in NADF. NADF were infected with adenoviral GFP-Hic-5 to overexpress Hic-5; adenoviral GFP served as a control. (5A) Cells were then lysed and lysates were resolved by 10% or 15% SDS-PAGE and transferred to nitrocellulose as described previously. Blots were probed for the indicated proteins; the results are represented as fold difference for (5B) cyclin A and (5C) p21. *$p<0.005$, n=3.
Figure 5B:
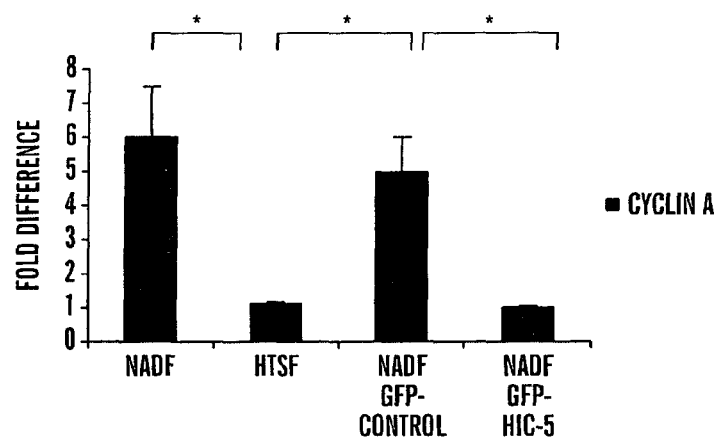
Figure 5C:
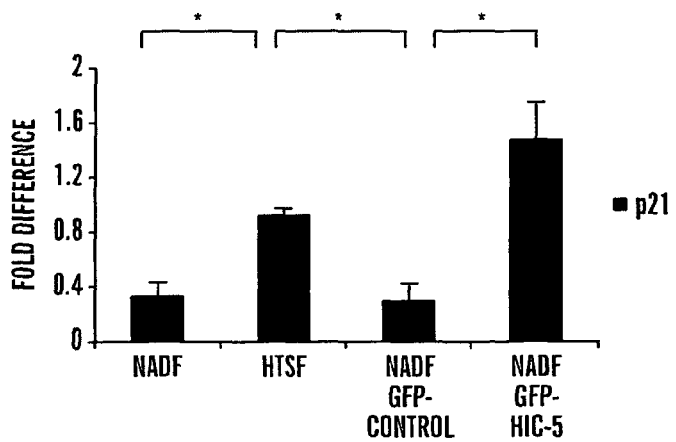

It was found that addition of TGF-β1 to NADF was sufficient to increase the expression of Hic-5 (FIG. 3a) and decrease the growth of NADF (FIGS. 1c and d). Therefore, whether or not overexpressing Hic-5 in NADF was sufficient to control cell cycle proteins under conditions in which adenovirus yielded greater than 90% infection efficiency was next determined. It was observed under these conditions that overexpressing Hic-5 in NADF resulted in a statistically significant 5-fold increase in the expression of $p21^{cip1}$ compared to GFP-control, and a statistically significant decrease in the expression of cyclin A as well as cyclin D1 to levels observed in HTSF (FIG. 5). These results confirm that Hic-5 controls the expression of key cell cycle proteins in NADF. It was next determined whether or not overexpression of Hic-5 resulted in its nuclear localization. Subcellular fractionation demonstrated that GFP-Hic-5 was localized in both the nucleus and the cytosol, and overexpressing Hic-5 also caused an increase in $p21^{cip1}$ levels in the nucleus compared to control.

Hic-5 is Downstream of the TGF-β1 Mediated Control Over Cell Cycle Progression in NADF and HTSF.

Figure 6A:
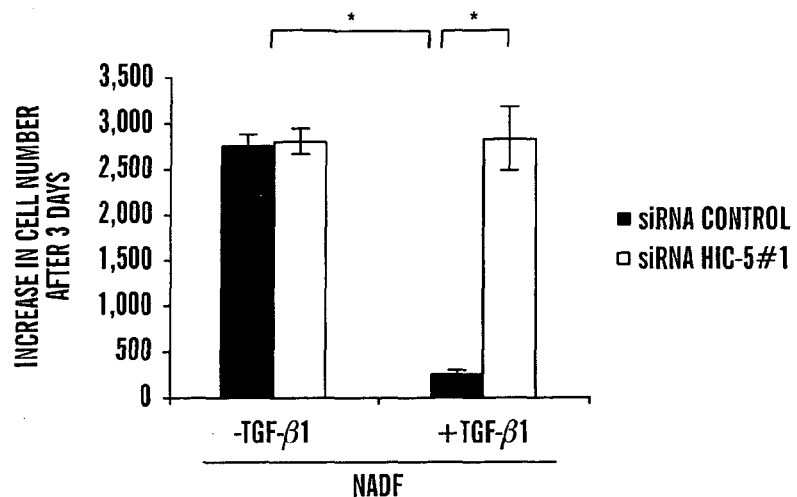
FIGS. 6(A)-(C): Either exogenous or autocrine TGF-β1 does not decrease proliferation in the absence of Hic-5. TGF-β1 (10 ng/ml) was added exogenously where indicated. (6A) NADF were transfected for 5 days with two separate siRNA Hic-5 duplexes (duplex #2, data not shown), or scrambled control. (6B) NADF were infected with adenoviral GFP-Hic-5 and GFP-control to overexpress Hic-5. (6C) HTSF were transfected for 5 days with two separate siRNA Hic-5 duplexes (duplex #2, data not shown), or scrambled control. siRNA Hic-5 transfected HTSF were infected for 24 hrs with either an adenoviral GFP-full length Hic-5 or control construct to rescue Hic-5 levels. Cell numbers were determined after 3 day incubation using CyQUANT® assay (increase in cell number at day 3 is calculated as; cell number at day 3 minus cell number at day 0). *$p<0.005$, n=3.
Figure 6B:
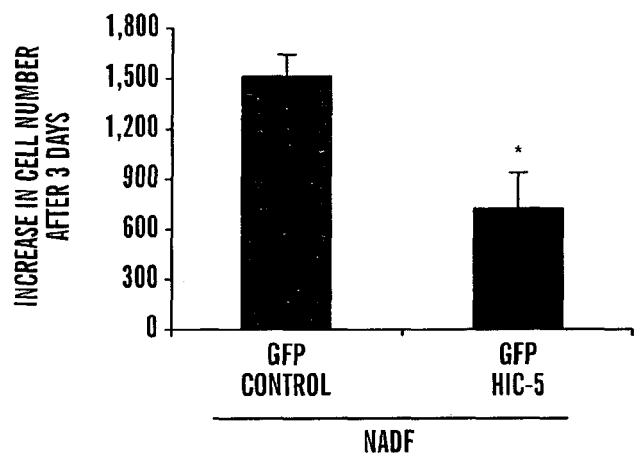

Since knocking down Hic-5 increased cyclin A and cyclin D1 levels in HTSF, and overexpressing Hic-5 in NADF decreased cyclin A and cyclin D1 levels, the growth potential of these cells under these conditions was next tested. As described above, the addition of TGF-β1 to NADF resulted in increased Hic-5 expression (FIG. 3a) and decreased cell growth (FIG. 1c); it was next determined whether inhibiting Hic-5 in turn disrupted the TGF-β1-mediated inhibition of NADF proliferation. NADF were transfected with either of two separate siRNA Hic-5 duplexes (duplex #2 yielded the same results as duplex #1) or with control siRNA. Cells were then cultured and the extent of Hic-5 knock-down confirmed (>90% reduction) and growth rates measured. Cells were seeded in serum containing media with or without the addition of TGF-β1 and cell number was determined on the third day as the increase in cell number from day 0 (cell number on day 3 minus the cell number on day 0). Time points taken at day 5 and day 7 yielded the same relative increase as day 3. It was observed that NADF knockdown for Hic-5, and TGF-β treatment did not exhibit decreased growth (FIG. 6a) compared to siRNA control in the presence of TGF-β1. To test whether or not Hic-5 was sufficient to regulate the proliferation of NADF these cells were transduced in the absence of siRNAs and TGF-β. It was observed that overexpressing Hic-5 with the adenoviral construct in NADF caused a significant decrease in proliferation compared to GFP-control (FIG. 6b). Cell numbers were determined at 0, 3, 5, and 7 days. The increase in NADF cell number occurring between day 0 and day 3 are shown (FIG. 6b). The increase in cell number at day 5 and day 7 yielded similar results.

Figure 6C:
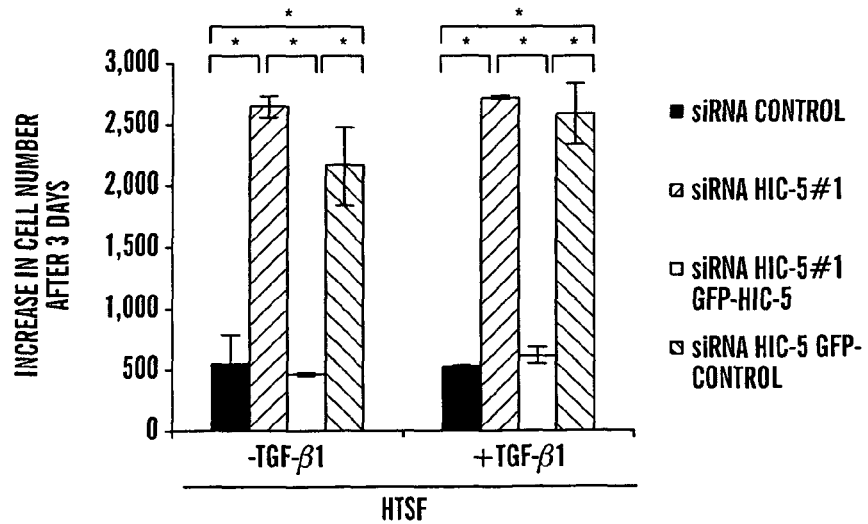

Next, the proliferation of HTSF in the absence of Hic-5 was examined HTSF were transfected either with two separate siRNA Hic-5 duplexes (duplex #2 yielded the same results as duplex #1) or with control siRNA. The extent of Hic-5 knockdown was confirmed (>90% reduction). After transfection, HTSF were seeded in serum containing media, with or without the addition of TGF-[3], and cell numbers were determined at 0, 3, 5, and 7 days. The increase in HTSF cell number occurring between day 0 and day 3 are shown (FIG. 6c). Increase in cell number at day 5 and day 7 yielded similar results. Knocking down Hic-5 increased the proliferation of HTSF, but importantly, the addition of exogenous TGF-β1 to these cells was not sufficient to override the ablation of Hic-5 and did not decrease the proliferation of HTSF, demonstrating that Hic-5 was necessary to mediate the TGF-β dependent proliferative effects in HTSF. Importantly, while knocking down Hic-5 in HTSF resulted in a marked increase in proliferation we also observed that rescuing the expression of Hic-5 by adenoviral infection was able to inhibit proliferation to levels observed in untreated HTSF (FIG. 6c). Taken together these data demonstrate that Hic-5 is both necessary and sufficient for TGF-β1 mediated modulation of fibroblast proliferation in pathogenic and normal fibroblasts.

Experimental Results

When skin is injured, quiescent fibroblasts migrate into the wound bed where they proliferate and differentiate into SMCA positive fibroblasts, termed myofibroblasts (Singer and Clark 1999). Myofibroblasts are contractile and synthetic cells that deposit abundant interstitial collagens, fibronectin and matrix-degrading proteases, thereby producing, contracting and remodeling the scar (Tomasek et al., 2002). While it is now clear that TGF-β1 is required for the terminal differentiation of myofibroblasts, its role in regulating fibroblast, and particularly myofibroblast, proliferation is unclear. During normal, acute wound healing, scar formation results from a finely regulated balance of proliferation and apoptosis (Singer and Clark 1999). Once the wound has healed and the scar formed (~day 14 in rodent models), the myofibroblasts decrease in numbers through apoptosis (Desmouliere et al., 1995). By contrast, in pathogenic scarring, such as hypertrophic scars, the myofibroblasts are present in the wound in relatively high numbers, for months to years after injury (Ehrlich et al., 1994). Their high numbers, in situ, along with their robust deposition of ECM proteins and hypercontractility are thought to be a central feature of pathogenic scarring (Tredget et al., 1997; Scott et al., 2000). Accordingly, HTS have been interchangeably referred to as fibroproliferative and fibrocontractive disorders (Grinnell 1994; Tredget et al., 1997; Scott et al., 2000). However, there have been surprisingly few studies that examine the regulation of cell cycle proteins in pathogenic fibroblasts, including HTSF. We demonstrate here that HTSF are in fact not hyperproliferating in comparison to NADF and proliferation seems to be negatively regulated by TGF-β1 in both NADF and HTSF, the latter through an autocrine loop. We find that in HTSF, Hic-5 is constitutively upregulated, due to a stable autocrine loop that produces and activates TGF-31. When we inhibit the autocrine loop of TGF-β1 in HTSF, we observe decreased expression of Hic-5 (FIG. 3a), decreased expression of p21$^{cip1}$ (FIG. 2a), and upregulation in proliferation to levels similar to NHDF (FIG. 1c). We can mimic the effect of the autocrine loop of TGF-β1 seen in HTSF, by exogenously adding TGF-β1 to NADF, and this results in the upregulation of Hic-5 (FIG. 3a), increased p21$^{cip1}$ levels (FIG. 2a) and subsequent decrease proliferative capacity (FIG. 1c). Importantly, when the expression of Hic-5 in HTSF is silenced by specific siRNAs, normal growth is restored in these cells (FIG. 6c). Transducing siRNA-treated HTSF with an adenoviral vector encoding mouse Hic-5 reverses this effect (FIG. 6c). When Hic-5 is overexpressed in NADF by adenoviral transduction, growth is markedly slowed, in the absence of TGF-β1 (FIG. 6b). These data demonstrate that TGF-β1 slows the proliferation of normal and pathogenic fibroblasts by a cellular mechanism in which Hic-5 is both necessary and sufficient.

The role of TGF-β1 in regulating fibroblast proliferation has been unclear for some time, in part because of differing reports in the literature (Thornton et al., 1990). These differences may be due to effects of varying TGF-β1 doses, to the source of fibroblasts assayed, or to the presence of other growth factors and cytokines in the cultures (Thornton et al., 1990). While others have reported that the autocrine production of TGF-β1 in adult HTSF leads to increased entry into S phase (Tredget et al., 2000), we found with pediatric HTSF that the autocrine loop mediated decreases in proliferation and entry into S phase. In accord with these findings we observed coordinated upregulation of p21$^{cip1}$ and downregulation of cyclins A and D1.

In a recent study, neonatal foreskin fibroblasts were infected with a recombinant retrovirus encoding a mutant form of TGF-β1 (cysteines 223 and 225 were converted to serines) that is secreted as a constitutively active molecule (Campaner et al., 2006). In this experimental system, TGF-β1 does not require activation and thereby mimics the autocrine loop seen in HTSF. These fibroblasts proliferate more slowly compared to control fibroblasts, in agreement with our findings (FIGS. 1c and 1d). These data leave open the possibility that pediatric/neonatal HTSF vs. adult HTSF respond differently to autocrine stimulation of TGF-β1. By demonstrating that Hic-5 is necessary and sufficient to regulate TGF-β1 effects on both NADF and HTSF proliferation, we believe that we have identified a central element in this regulatory mechanism. Analysis of the signaling networks that govern Hic-5 expression and traffic to and from the nucleus may account for differences in the effects of TGF-β1 on proliferation of mesenchymal cells taken from a variety of tissues and cultured under a variety of conditions.

Hic-5 is a TGF-β1- and $H_2O_2$-inducible gene product with homology to paxillin (Shibanuma et al., 1994; Thomas et al., 1999). It is expressed in platelets and mesenchymal cells, such as fibroblasts and smooth muscle cells (Hagmann et al., 1998; Yuminamochi et al., 2003). It is not present in epithelial cells, but is upregulated in cells undergoing an epithelial-to-mesenchymal cell transition (Tumbarello et al., 2005; Tumbarello and Turner, in press). To date, the regulation or the function of Hic-5 in HTSF or other fibrotic disorders has not yet been studied. Hic-5 localizes to both the focal adhesions (Thomas et al., 1999) and in the nucleus (Shibanuma et al., 2003). Recent data also demonstrated that suppression of Hic-5 by specific siRNA in epithelial cells undergoes EMT, decreased RhoA activation in concert with the failure of TGF-β to stimulate actin stress fibers and focal adhesion formation (Tumbarello and Turner, in press). Previously we demonstrated that HTSF constitutively express supermature focal adhesions and the generation of supermature focal adhesion occurs through TGF-β1 regulation. Cells that contained these larger adhesions bound tighter to plasma fibronectin and had higher contractile activity, as measured by collagen contraction (Dabiri et al., 2006). Determining whether or not Hic-5 regulates the generation of supermature focal adhesions will be crucial to understanding important aspects of pathogenic myofibroblasts.

Our data reported here demonstrate that Hic-5 is markedly upregulated and readily localizes to the nucleus of HTSF due to the autocrine loop of TGF-β1 (FIGS. 3a and 3b). Others have reported that Hic-5 transactivated the p21 promoter through two of five Sp1 sites in the region proximal to the TATA box. The Hic-5 effect was mediated by a transactivation domain of Sp1 and functional interaction with p300 through its LIM4 domain. Hic-5 was also shown to interact functionally and physically with Smad3 through its LIM domains and to potentiate p21 promoter activity together with Smad3 and Sp1. Thus, Hic-5 may function as a cofactor in the transcriptional complexes that contain Sp1, playing a role in gene transcription in the nucleus (Shibanuma et al., 2004). Therefore, it is important to determine whether Hic-5 could activate the transcription of other genes that are involved in mediating the fibrotic phenotype and these studies are currently underway in our laboratory.

The data reported here focus on an important role for Hic-5 in pathogenic fibroblasts in slowing cell proliferation in response to TGF-β1. HTSF have been previously shown to be resistant to apoptosis through the upregulation of bcl-2 (Moulin et al., 2004); others have demonstrated that TGF-β1 has anti-apoptotic effects (Zhang and Phan 1999). Consistent with this model, we find that the HTSF used in our study also upregulate bcl-2, and do not readily undergo apoptosis compared to NADF (data not shown).

In conclusion, TGF-β1 mediates a slowing of normal dermal fibroblast proliferation and may represent a critical early step in myofibroblast differentiation. The dampened proliferation that we observe in HTSF is mediated by an autocrine loop in which active TGF-β1 is produced. In NADF and HTSF, the TGF-β1-dependent effects on proliferation are mediated by a mechanism in which Hic-5 is both necessary and sufficient. We believe that these findings provide a new avenue for research on the pathogenic myofibroblast phenotype as it occurs in HTSF and potentially other fibrotic skin diseases.

Example 2

Hic-5 Promotes the Hypertrophic Scar Myofibroblast Phenotype by Regulating the TGF-β1 Autocrine Loop Hic-5 is Necessary for the Maintenance of Supermature Focal Adhesions in HTSF.

Figure 7A:
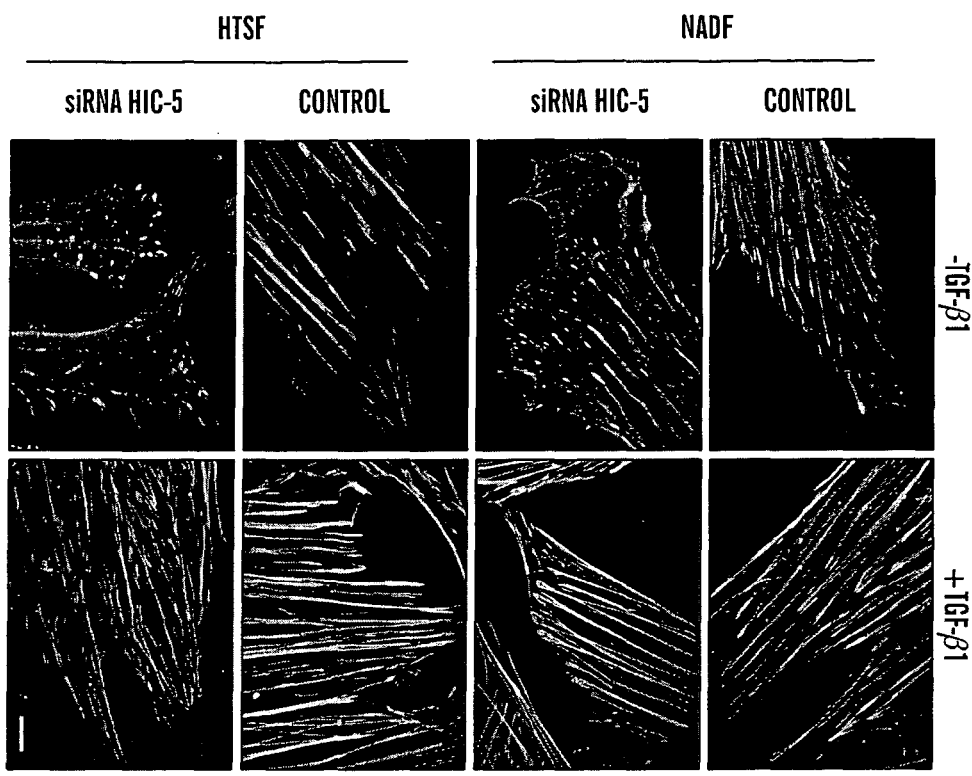
FIGS. 7(A)-(B): Hic-5 helps to maintain the persistence but not the generation of supermature focal adhesions. Cells were transfected with either siRNA to Hic-5 or scrambled control. After transfection, cells were trypsinized and replated in complete media for 18 hours, then washed with PBS and serum-free medium was added with or without the addition of TGF-β1 (10 ng/ml) for five days. (7A) Cells were then stained for vinculin (green) and stress fibers (red). (7B) Percent focal adhesions greater than 6 µm² was calculated as a ratio of the total number of focal adhesions greater than 6 µm² divided by the total number of focal adhesions multiplied by 100. *$p<0.005$, n=3. Bar=10 µm.
Figure 7B:
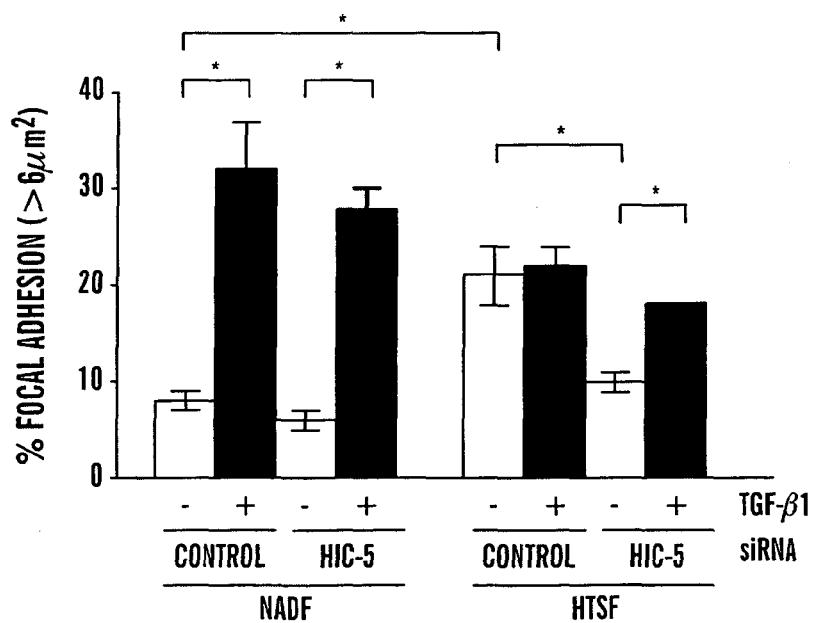
Figure 8A:
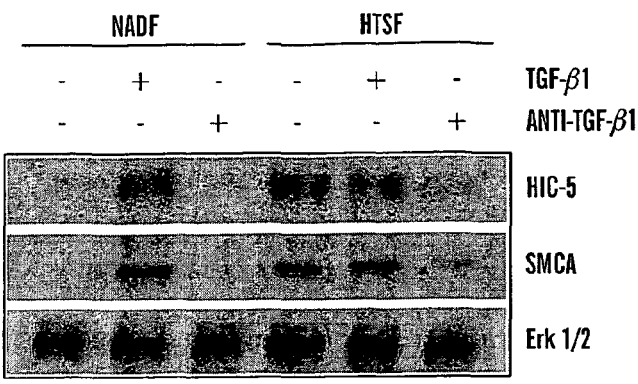
FIGS. 8(A)-(E): Hic-5 maintains the expression of SMCA in HTSF but TGF-β1 is necessary for initiating fibroblast differentiation. (8A) Cells were plated for 18 hrs in serum-containing medium then, washed with PBS and serum-free medium was added with or without the addition of TGF-β1 (10 ng/ml) or anti-TGF-β1 (20 µg/ml). Cells were then lysed and directly resolved by SDS-PAGE gel (10%) and analyzed by western blot. The intensity of each band was normalized, first for differences in protein loading using Erk1/2, and then to HTSF for each condition. The results are represented as fold difference for (8B) SMCA and (8C) Hic-5 expression. Data from replicate experiments were pooled and presented relative to HTSF control (n=4). (8D) Cells were transfected with siRNA and replated as described in FIG. 1, with slight modification; after five days, cells were lysed, and lysates were resolved by SDS-PAGE gel (10%), analyzed by western blot and quantitated as described above. *p<0.005, n=3. (8E) represents the fold difference in SMCA expression.
Figure 8B:
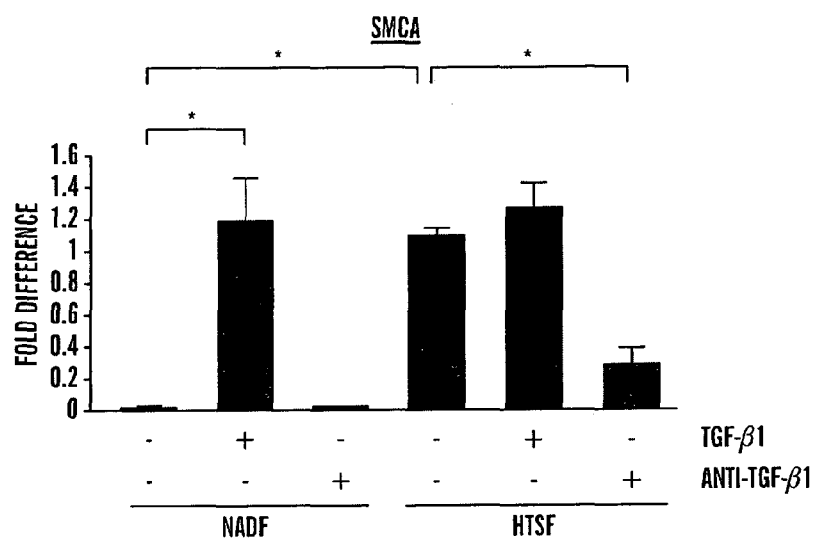
Figure 8C:
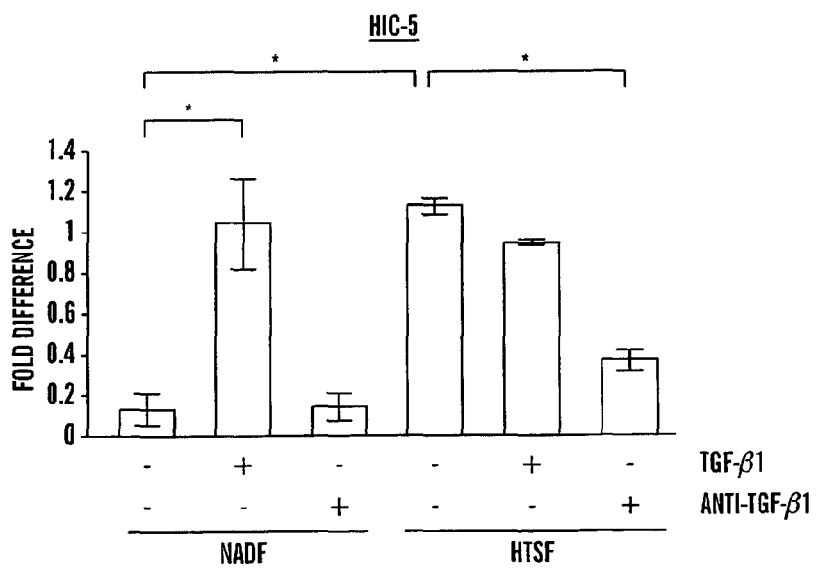
Figure 8D:
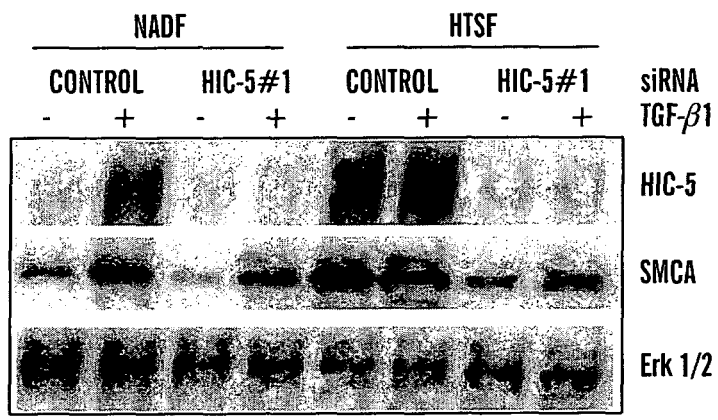
Figure 8E:
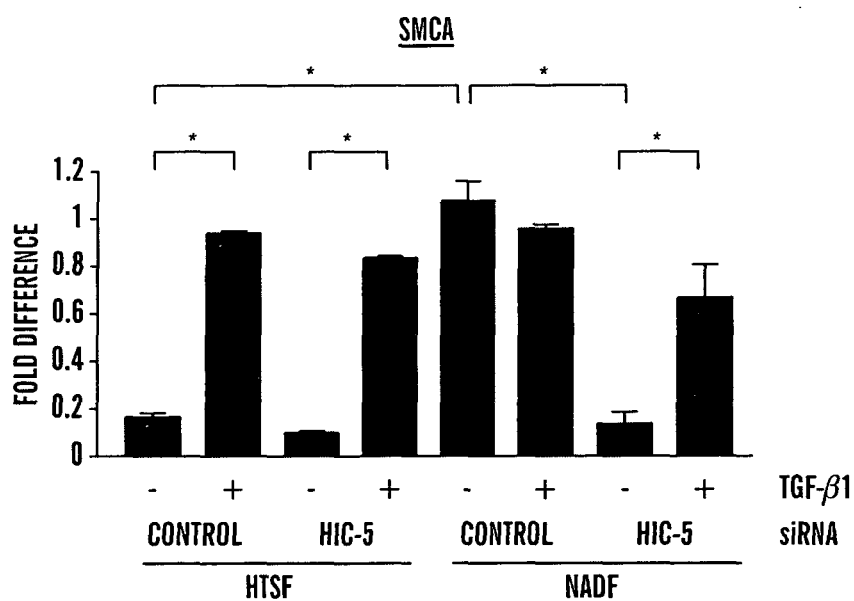

HTSF persistently express a higher percentage of supermature focal adhesions ($\geq 6 \mu m^2$) per cell compared to NADF and their persistence of these focal adhesions in HTSF was maintained by the elaboration of an autocrine loop generating active TGF-β1 (Dabiri et al., 2006). It was determined how TGF-β1 maintained these supermature focal adhesions in HTSF. To do so, either Hic-5 or control siRNAs were transfected into either HTSF or NADF. Cells were then trypsinized and cultured in the presence or absence of TGF-β1 (10 ng/ml) for 5 days. These cells were fixed, stained with anti-vinculin and the areas of focal adhesions measured. Western blot analysis of Hic-5 was also performed to determine that siRNA to Hic-5 was effective in decreasing Hic-5 levels in NADF and HTSF (FIG. 8B). It was found that 20% of the focal adhesions in HTSF measured greater than 6 $\mu m^2$ compared to approximately 7% seen in NADF. The addition of TGF-β1 to NADF resulted in a nearly 10-fold increase in the percentage of focal adhesions greater than 6 $\mu m^2$. It was further found that upon genetic silencing of Hic-5 in HTSF, a significant decrease in the percentage of focal adhesions greater than 6 $\mu m^2$ was observed. Since TGF-β1 regulates the size of focal adhesions, it was determined whether or not Hic-5 was necessary for this TGF-β1-dependent effect. In the absence of Hic-5, addition of TGF-β1 increased the size of focal adhesion to levels comparable to control siRNA in the presence of TGF-β1 in NADF. Interestingly, in the absence of Hic-5, but with the addition of exogenous TGF-β1 to HTSF, focal adhesion areas were restored to those of control HTSF. While genetic silencing of Hic-5 in HTSF decreased the area of focal adhesions, it did not alter the overall levels of vinculin or paxillin expressed. These results indicate that Hic-5 is important for maintaining the persistence of supermature focal adhesions, but is not required for their generation by TGF-β1 (FIG. 7).

Hic-5 is Important for the Maintenance of SMCA Expression but not the Generation of SMCA by TGF-β1.

TGF-β1 is important in the transition from fibroblast to myofibroblast, and in culture this differentiation occurs over the course of five days (Desmoulière et al., 1993). Since it was earlier discovered that Hic-5 is regulated by TGF-β1 and that Hic-5 is important for the maintenance of supermature focal adhesions in HTSF, it was of interest to determine whether Hic-5 levels are maintained during the course of the five day transition from a fibroblast to differentiated myofibroblast. Either NADF or HTSF were cultured in serum free media for five days with or without the addition of TGF-β1 (10 ng/ml) or anti-TGF-β1 (20 µg/ml). It was found that HTSF were constitutively myofibroblastic, expressing SMCA persistently; Hic-5 expression was also maintained in HTSF during five days in serum free media (FIG. 8A). With the addition of TGF-β for five days, both SMCA and Hic-5 were upregulated in NADF to levels comparable to HTSF control. Addition of anti-TGF-β1 to HTSF cultures decreased the expression of both Hic-5 and SMCA (FIG. 8A) indicating that the autocrine loop of TGF-β1 maintained the expression levels of both SMCA and Hic-5. Since Hic-5 regulated the maintenance, but not the generation, of supermature focal adhesions in HTSF, and because there is a link between SMCA, intracellular tension, and focal adhesion development (Hinz, 2007), it was next determined if inhibition of Hic-5 regulated SMCA expression. Either Hic-5 or control siRNA were transfected into HTSF and NADF for 5 days. Cells were trypsinized and replated in serum-free medium in the presence or absence of TGF-β1 (10 ng/ml) for 5 days. We found that genetic silencing Hic-5 decreased the expression of SMCA in HTSF. In NADF or HTSF treated with Hic-5 siRNA, TGF-β1 was still able to increase the expression of SMCA to levels as high as those of HTSF controls (FIG. 8B). These results indicate that Hic-5 is important for maintaining the persistence of SMCA expression, but is not required for the initial generation of SMCA expression. Cells were also immunostained for SMCA, to ensure that the differences in protein expression levels observed by western blotting (FIG. 8B) correlated with SMCA assembled into stress fibers. It was found that approximately 80% of the HTSF were in fact SMCA-positive and that the inhibition of Hic-5 decreased the percent of SMCA-positive cells by 8-fold to 10%. The addition of TGF-β1 to HTSF in which Hic-5 was genetically ablated resulted in a 5-fold increase in the percentage of positive SMCA cells. In NADF, the addition of TGF-β1 increased the percent positive SMCA cells by 7-fold and in the absence of Hic-5 the addition of TGF-β1 was still able to increase SMCA to levels comparable to NADF control siRNA. These data indicate that Hic-5 is important in maintaining the persistence of SMCA in HTSF, however it is not necessary for SMCA generation or assembly into stress fibers.

Hic-5 Regulates the Expression of ECM Proteins and Modulates the Ability of HTSF to Contract Collagen.

Figure 9A:
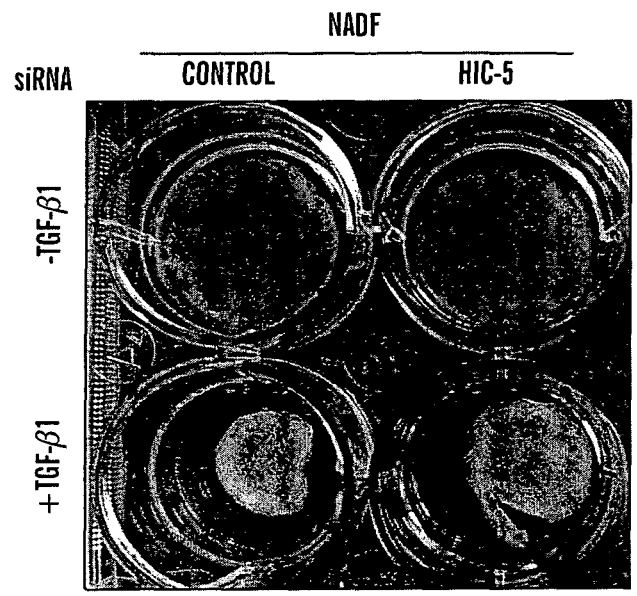
FIG. 9 (A)-(D): Hic-5 maintains HTSF ability to contract collagen and produce ECM proteins. Cells were transfected with Hic-5 siRNA and replated as described in FIG. 1, with slight modification, and harvested after five days. (9A) NADF or (9B) HTSF were trypsinized and cultured in a collagen lattice, rimmed, and covered with serum-free medium for three days. For NADF (9C) and HTSF (9D), the percent from initial diameter was measured as the ratio of the decrease in diameter divided by the original diameter at day 3 multiplied by 100. *p<0.005, **p<0.05, n=3. (9C) Cells were transfected with siRNA and replated for western blot analysis as described in FIG. 2B, with slight modification; cells were lysed, and lysates were resolved by SDS-PAGE gel (8%) and analyzed by western blot. *p<0.005, n=3.
Figure 9B:
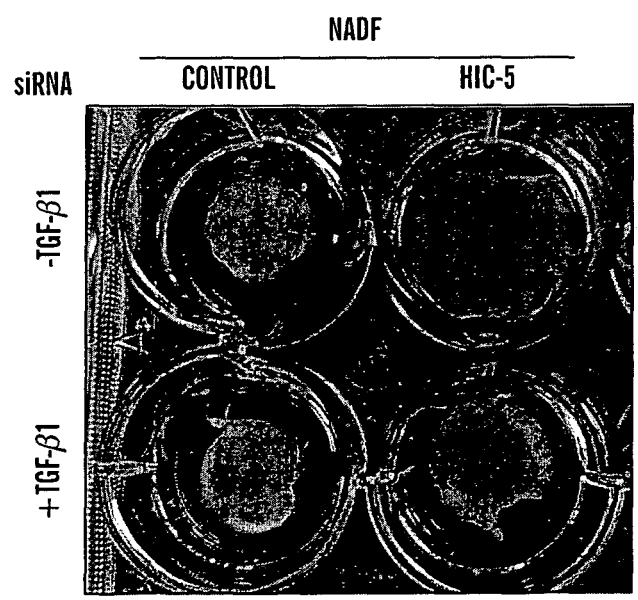
Figure 9C:
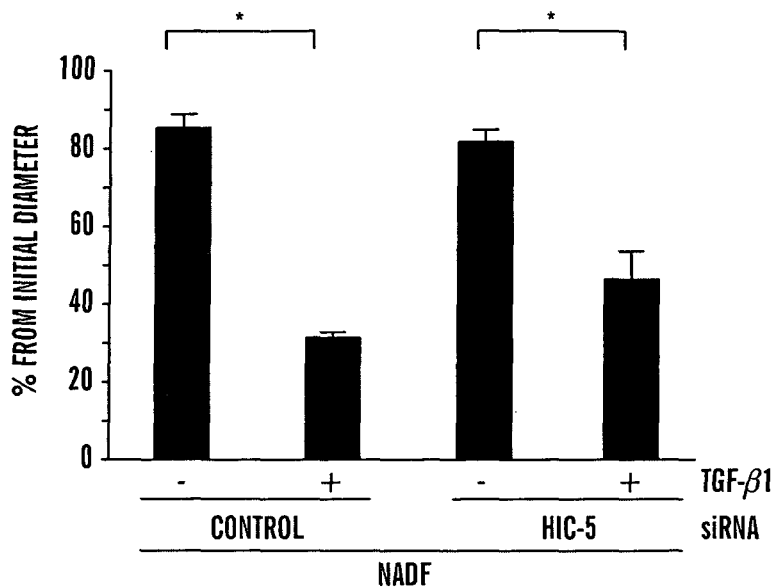
Figure 9D:
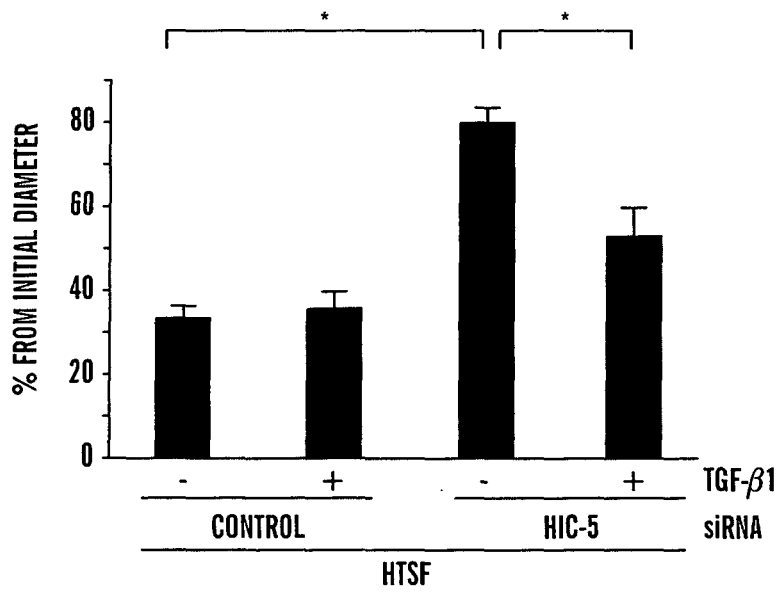

SMCA-positive fibroblasts are important in wound closure due to their ability to contract the matrix, a function that has been modeled in vitro using collagen contraction assays (Grinnell, 1994). Since knocking down the expression of Hic-5 decreased SMCA levels, it was next determined whether or not the inhibition of Hic-5 disrupted the ability of HTSF to contract collagen. Either Hic-5 or control siRNA were transfected into either HTSF or NADF. Cells were trypsinized and cultured in serum-free medium in the presence or absence of TGF-β1 (10 ng/ml) for 5 days. Cells were then cultured in a floating collagen lattice for three days (FIGS. 9A and 9B). Western blots were performed on cell lysates to confirm that siRNA to Hic-5 was effective in decreasing Hic-5 levels in NADF and HTSF (FIG. 9C). It was found that HTSF contract collagen more extensively (3-fold) compared to NADF (FIGS. 9A and 9B). The addition of TGF-β1 to NADF decreased the collagen diameter by 3-fold, comparable (FIG. 9A) to contraction observed with HTSF treated with control siRNA (FIG. 9B). When Hic-5 was silenced in NADF in the presence of TGF-β1, NADF were still able to contract collagen (FIG. 9A). Knocking down the expression of Hic-5 resulted in a decrease in the ability of HTSF to contract collagen (FIG. 9B). However, the addition of TGF-β1 fully rescued the ability of HTSF to contract collagen (FIG. 9B), indicating that Hic-5 is important in maintaining HTSF collagen contraction activity, but it is not necessary for the generation of contraction in HTSF or NADF.

TGF-β1 induces the expression of collagen and FN in fibroblasts and Hic-5 over-expression increases the mRNA levels of certain ECM proteins (Shibanuma et al., 1997). It was next tested whether or not Hic-5 regulates the expression of FN and collagen type I in HTSF and/or NADF (FIG. 9C). Either Hic-5 or control siRNA was transfected into HTSF or NADF, cells were trypsinized and cultured in the presence or absence of TGF-β1 (10 ng/ml) for 5 days. It was found that HTSF expressed approximately 3-fold more collagen and FN compared to NADF. The addition of TGF-β1 significantly increased the expression of these ECM proteins in NADF to levels comparable to HTSF. Interestingly, treatment of HTSF with Hic-5 siRNAs resulted in a decrease in collagen and FN expression. The addition of TGF-β1 to NADF in the absence of Hic-5 was not able to increase the expression of collagen, but did significantly increase the expression of FN, albeit not to control levels, indicating that Hic-5 is required for the TGF-β1 induction of collagen (FIG. 9C). However, the partial restoration of FN expression by TGF-β1 in the absence of Hic-5 indicates that FN expression may be regulated by two pathways one dependent upon, and the other independent of, Hic-5.

The experiments described tested the role of Hic-5 in maintaining and establishing the HTSF phenotype. We were also interested in testing whether or not Hic-5 was sufficient to cause the differentiation of fibroblasts to myofibroblasts without the presence of TGF-β1. To test this, NADF were infected with adenoviral constructs expressing either GFP control or GFP-Hic-5 for five days in serum-free medium. It was found that cells in which Hic-5 was overexpressed were unable to increase the size of focal adhesions and the expression of SMCA, as well as to induce the contraction of collagen, and to increase the expression of collagen or FN (not shown). These results indicated that Hic-5 was not sufficient to drive the fibroblast to myofibroblast differentiation.

Hic-5 Regulates the Autocrine Loop of TGF-β1 in HTSF.

Figure 10B:
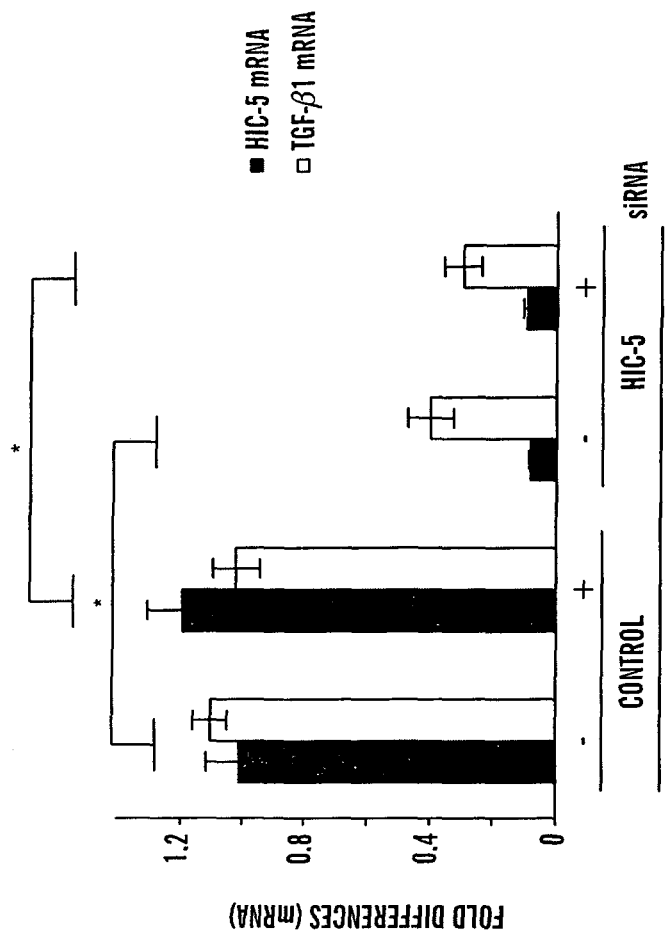
FIGS. 10(A)-(E): siRNA Hic-5 disrupts the autocrine loop of TGF-β1 in HTSF. Cells were transfected with Hic-5 siRNA and replated as described in FIG. 1, with slight modification and harvested after five days. (10A) total RNA was isolated from HTSF and RT-PCR was performed to compare TGF-β1 and GAPDH mRNA levels relative to untreated HTSF, or (10B) conditioned medium was collected from the samples without added TGF-β1 and sandwich ELISA using an antibody reactive with active TGF-β1 was performed on conditioned media to measure (10D) the amount of active TGF-β1 and (10E) the amount of total TGF-β1 (acid treated to activate the latent-TGF-β1). (10C) Amounts of latent-TGF-β1 were determined by subtracting levels of active TGF-β1 from total TGF-β1. *p<0.005, n=3.
Figure 10A:
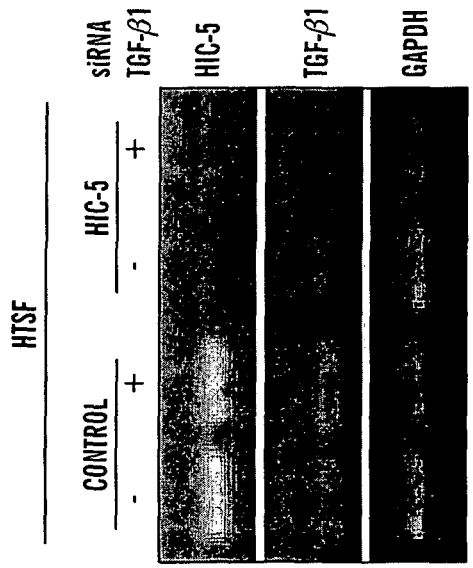
Figure 10E:
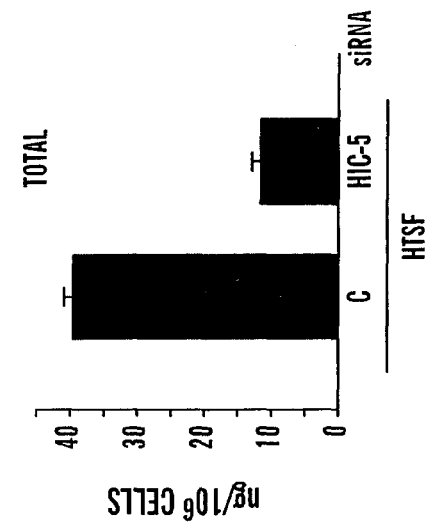
Figure 10D:
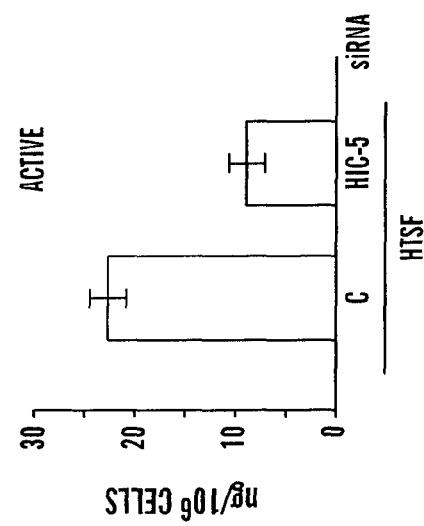
Figure 10C:
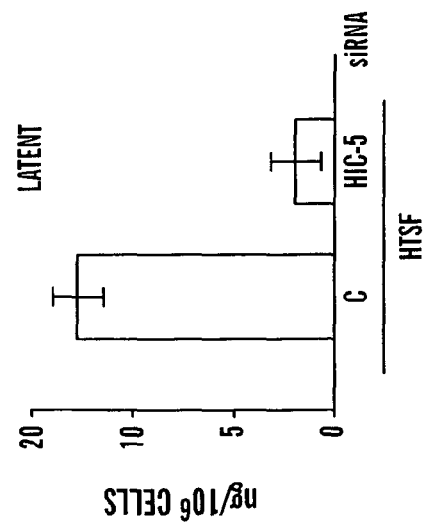

When Hic-5 was silenced with specific siRNA in HTSF, these pathogenic cells reverted to a resting fibroblast phenotype and the addition of TGF-β1 caused the differentiation of these resting fibroblasts back to a myofibroblast phenotype. Thus, Hic-5 is regulating the autocrine loop of TGF-β1 in HTSF. Either Hic-5 or control siRNA were transfected into HTSF, cells were then trypsinized and replated in serum-free medium for five days with or without the addition of TGF-β1 (10 ng/ml). Conditioned medium was then collected from cells that were not treated with exogenous TGF-β1. RNA was isolated from all cells and RT-PCR was performed to compare the mRNA levels of TGF-β1. It was found that knocking down Hic-5 resulted in decreased TGF-β1 mRNA levels (FIG. 10). The addition of exogenous TGF-β1 did not increase TGF-β1's own mRNA expression (FIG. 10A). To test TGF-β1 protein levels, conditioned medium was assayed using a sandwich ELISA. It was found that both the amount of active and total (obtained after acid activation of the conditioned media) was decreased in the siRNA Hic-5 transfected HTSF (FIG. 10B). These findings demonstrated that autocrine production of TGF-β1 was regulated by Hic-5. Whether or not overexpressing Hic-5 had any effect on TGF-β1 production, secretion, or activation was also tested. NADF were transfected with GFP-Hic-5 or GFP-control for five days in serum free conditions, and RNA and conditioned medium was isolated after the fifth day. Overexpressing Hic-5 increased the mRNA levels of TGF-β1 and the amount of secreted latent-TGF-β1, but it did not increase the amount of active TGF-β1. These results demonstrate that Hic-5 is both necessary and sufficient to regulate the production of, but not the activation of, TGF-β1.

These studies show that Hic-5 is necessary for maintaining the perpetual myofibroblast phenotype seen in HTSF by virtue of its regulation of endogenous TGF-β1 production. However it is not sufficient to drive fibroblast differentiation to myofibroblast in NADF. These data are the first to show a critical component in the mechanism through which the autocrine loop in HTSF is maintained resulting in the pathogenesis of HTS.

Experimental Results

TGF-β1 is a critical regulator of myofibroblast generation and function and we and other workers postulate that myofibroblast persistence in fibrotic lesions results from the self-production and activation of TGF-β1, through an "autocrine loop" (Dabiri et al., 2006; Dabiri et al., in press; Hinz, 2007). Tredget et al. (2000) reported that hypertrophic scar tissues and fibroblasts produce more TGF-β1 mRNA and protein than normal skin and cells. We determined that the autocrine production of TGF-β1 in HTSF, resulted in constitutively larger focal adhesion compared to NADF (Dabiri et al., 2006). These larger adhesions, mediated tighter binding to plasma FN, and enhanced collagen contraction to a greater extent in HTSF compared to NADF. Recently, we reported that persistent TGF-β1 expression through an autocrine loop slowed HTSF cell proliferation (Dabiri et al., in press).

In the present study we identify a critical element, the focal adhesion protein Hic-5, in the autocrine production of TGF-β1 and the persistent myofibroblast phenotype seen in HTSF. Genetic silencing of Hic-5 resulted in the decreased size of focal adhesions in HTSF, as well as decreased expression of SMCA, collagen contraction, collagen and FN expression as well as attenuation of the autocrine production of TGF-β1 in HTSF. Our data demonstrate that Hic-5 is an essential element in the mechanism driving autocrine TGF-β1 production. Interestingly, forced expression of Hic-5 in NADF was not sufficient to promote myofibroblast differentiation but did increase the steady-state levels of TGF-β1 mRNA. Accordingly, these cells secreted significantly more latent-TGF-β1 but did not increase the levels of active TGF-β1 in the conditioned medium (data not shown). These data indicate that Hic-5 is directly involved in regulating latent TGF-β1 expression while its role in regulating TGF-β1 activation is not known.

Hic-5 is upregulated in cells undergoing an epithelial-to-mesenchymal cell transition (EMT) and is necessary for this phenotypic conversion (Tumbarello et al., 2005; Tumbarello and Turner, 2007). Forced overexpression of Hic-5 in the mammary epithelial, MCF10A, cell line led to a disruption of the cortically arranged actin and the development of ROCK-dependent stress fibers indicative of a contractile mesenchymal phenotype (Tumbarello and Turner, 2007). Silencing Hic-5 mRNA with specific siRNAs suppressed TGF-β1-dependent RhoA activation during EMT. However, we find that in the absence of Hic-5, with the addition of TGF-β1, NADF could still differentiate into a myofibroblast and, conversely, that overexpressing Hic-5 in NADF was not sufficient to cause fibroblast differentiation (FIG. 8B and data not shown). Therefore, we hypothesize that Hic-5 is required to properly regulate a set of Rho modulators (GEFs and GAPs) required for EMT that is distinct from those required for myofibroblast differentiation. This hypothesis has important implications for EMT during tumor progression and as a potential source of fibroblasts at sites of tissue injury.

Our earlier work established both that an autocrine loop exists for TGF-β1 production and activation in HTSF and that this autocrine loop regulates the proliferation of these pathogenic myofibroblasts in a Hic-5-dependent mechanism (Dabiri et al., 2006; Dabiri et al., in press). We now report that Hic-5 maintains the autocrine loop of TGF-β1, which in turn leads to the maintenance of the myofibroblast phenotype. Importantly, we find that the TGF-β1-dependent autocrine loop is disrupted when Hic-5 is knocked down, resulting in the reversion of these myofibroblasts to a more normal fibroblast phenotype. Adding back active TGF-β1 to RNAi-treated HTSF restores most myofibroblast functions (FIGS. 7-9) but not the autocrine loop (FIG. 10). Our data suggest that Hic-5 is an important new target in HTSF, and potentially other pathogenic myofibroblasts, that could be inhibited therapeutically to help in the treatment of cutaneous fibrosis, and possible other fibrotic disorders.

Example 3

Experimental Plan for Wound Healing in Animal Models

For each experiment the animals (mice or rats) are randomly divided into two experimental groups of 6 animals each: (1) wounded and treated with control (vehicle alone); (2) wounded and treated with agent (i.e., Hic-5 antagonist such as Hic-5 siRNA or a pharmacological drug). Each of these two treatment groups are randomly divided again into 2 sub-groups, representing two time points (3 animals each). To ease sample handling, the time course is done as four separate experiments. In the first experiment, two healing intervals are studied (0, 2 days) and animals are treated with IgG's on day 0. In the second experiment, healing intervals of 4 and 6 days are done with animals infused on day 0 and days 4, respectively. In the third experiment, healing intervals are 8 and 10 days with infusion on 0, 4 days. In the fourth experiment, healing intervals are 14 and 28 days with infusion again on 0, 4 days and potentially 8 days.

At day=0, all animals are anesthetized and receive full thickness excisional wounds using a 4 mm diameter sterile biopsy punch at 4 separate sites on the dorsum of each of three animals to control for cranial-caudal differences in wound healing. The locations of wounds are encoded in a blinded fashion so that subsequent comparisons are controlled for anatomic differences in healing. A concentric circle of fluorescent dye (diI) is placed 2 mm outside of each wound, against which wound contraction will be measured.

For some fibrotic models (for example, Tsk2 mice which get a progressive scleroderma-like fibrotic disorder, Tsk1 mice, bleomycin treated mice, or other fibrotic animal model known to those of skill in the art) no wounds are made. Instead fibrotic skin is harvested from mice at intervals of 1- and 4 months after birth (Abraham & Varga, TrendsImm '05). Animals will be treated or not as described below.

Treatment regimen (siRNA): In these experiments, animals are treated by intra-dermal or intra-wound injection of siRNA, either unmodified or modified with cholesterol (Soutschek et al, 2004). A recent report demonstrated comparable knockdown in skin with either modified or unmodified siRNAs (Wang et al, 2007). In brief, at intervals after wounding, a total volume of 50 ul phosphate-buffered saline containing 20 ug siRNA is injected into wounds or into flanking dermis. These inhibitors have been demonstrated to be effective for at least 5 days (Wang et al, 2007).

Treatment regimen (drugs): Animals are treated systemically with drugs by administering them intraperitoneally, as follows: Y27632 (30 mg/kg), Apocyanin (10 mg/kg) or Fe-TBAP (5 mg/kg) at daily intervals for the duration of the treatment period (14 days) (Muratata et al J. Surg Res, 2003; Melov et al, J. Neuro, 2001; Saito et al, MolVis, 2007).

Tissue harvest and fixation: Animals are housed individually and inspected daily to insure that no morbidity has resulted from either the surgery or treatment. Two hours before euthanasia, animals are injected subcutaneously with 5-bromo-2'-deoxyuridine (BrdU) to permit analysis of cell proliferation. At the designated interval of healing the animals are killed under anesthesia for subsequent biochemical and histological analyses.

The tissue samples to be harvested are coded by the investigators at the outset of this blinded study. A single group of animals consisting of triplicate animals in each of 4 treatment groups (control; drug; two time points), 4 bisected wounds per animal, yielding 12 samples for cryostat and 12 samples for paraffin sections or 96 blocks for each experiment. For all quantitative assays discussed below, mean values (+/−standard error) are calculated for each group, the data then unblinded and comparisons of treatments groups done using two-way analysis-of-variance. A "p value" of less than 0.05 will be considered significant.

Ample skin around, and including, each wound is excised and pinned out flat in fixative for a short interval. A digital brightfield/fluorescent photograph of the wound site and the fluorescent outer circle is taken. The wounds will be bisected and the cross-sectional (internal) faces marked with a dot of India ink for proper orientation (carbon facing out) in the blocks during the embedding process so that sections are prepared from the center of the wound. The bisected specimen is then be fixed overnight in cold 4% paraformaldehyde in PBS. To stain for active Caspase-3 in tissue sections it will be necessary to fix a portion of the tissue in acetone (see "Apoptosis" below) rather than paraformaldehyde. For cryopreservation, fixation of one half of the bisected tissue will be quenched with glycine. The piece will then be infiltrated with 30% cold sucrose for 18 hrs and snap frozen in OCT compound on dry ice. The other half of the bisected wound will be used for paraffin histology.

DATA ANALYSIS. Sections from paraffin blocks from each treatment groups of animals are stained with either Hematoxylin and Eosin (H&E) or Massons trichrome and studied for marked changes in cytologic features and tissue structure.

These sections are analyzed with several overlapping phases of wound healing in mind: Inflammatory phase (~days 0-4); Epidermal migration (~days 0-4); Granulation tissue formation (~days 4-6); and, Scar formation (~day 6 and later).

Inflammatory phase: The numbers of neutrophils in H&E sections are quantitated using their characteristic nuclear morphology. A comparison of day 0 and day 1 animals, treated or not, will indicate whether, and to what extent, treatment alters neutrophil infiltration in healing wounds. The neutrophils are enumerated (per high power field) at 1 day post-wounding using their characteristic morphology. Should differences between animals be observed as early as day 1, shorter time points (hrs.) will be included to determine how early the effect occurs. Of course, specific functions of neutrophils may be affected and we will be watchful for morphological clues (e.g., excessive pycnotic nuclei, abcesses, etc) that might indicate an alteration in cell function. Because cytologic features, such as nuclear morphology, are more difficult to distinguish for mononuclear phagocytes, than for neutrophils, immunoperoxidase staining with antibodies specific for animal monocytes will be carried out. The number of immunopositive cells per high power field (40×) will be determined and correlated with treatment group.

Epidermal migration: Possible effects of treatment on epidermal migration will be determined by quantitating the percentage of the wound area covered by epidermis from digital images at the gross level. Epidermal cross-sectional area from H&E stained sections taken from the center of fixed, bisected wounds will also be quantitated. The data will be expressed as the percentage of the wound covered by epidermis using image analysis programs.

Granulation tissue formation: Any influence of the proposed treatments on angiogenesis will be determined by quantitating the percentage area of the wound occupied by granulation tissue (at day 4-10) from H&E stained sections using image analysis software. We will analyze cryosections and enumerate vessel profiles from the center of wounds taken from treated or control animals using specific markers of angiogenesis including immunohistology for CD31 (PE-CAM), vonWillebrand factor and type IV collagen.

Scar formation: We will analyze sections for changes in the overall structure of collagen bundles within wounds that are stained blue in trichrome-stained sections. Using coded samples, we will analyze slides from day 4, 6, 8, 10, 14, 28 time points. In normal wounds, deposited scar collagen has a distinctive linear pattern, differing significantly in morphology from the "basket weave" morphology of normal dermis. We will complement the trichrome stained sections with additional specimens prepared for polarization microscopy. Data resulting from this blinded study will be uncoded and compared for animals from either treatment group.

Breaking-strength measurements on incisional wounds will also be performed with tensile strength measurements. Linear incisions on the dorsum will be carried out; the contralateral dorsal side will be left unwounded. The animals will be euthanized at either 6, 10, 14, 28 days post-wounding. Strips of tissue will be harvested, but not fixed in formalin, and subjected to breaking strength measurements. The data will be normalized for scar width and expressed as grams/$mm^2$. A "t test" will be performed ($p<0.05$) to test our hypothesized differences in wound strength. Care will be taken to account for variability due to anatomic position.

Cell activation, proliferation and death: We will analyze wounds for the appearance of SMC α-actin positive cells. We have already observed that the percentage of these cells increases markedly at day 4 and decreases after 10 days following wounding. For SMC α-actin immunostaining, we will use anti-SMC α-actin Mab (1A4, Dako) followed by affinity purified goat anti-mouse IgG, and for nuclear labelling, Hoechst 33342. This double labelling protocol, will allow us to calculate the percentage of total cells which are SMC α-actin positive. We recognize that identification of fibroblasts by morphological criteria in tissue sections will yield three classifications: (1) those cells which have clear morphologic features (e.g., elongated cells); (2) those which are likely fibroblasts, but could be other cell types; and, (3) those which clearly are not fibroblasts (endothelial cells, vascular smooth muscle cells). All SMC α-actin positive cells in the wound bed will be quantitated, avoiding the brightly staining vascular smooth muscle cells that are obvious by their presence in the medial layer of arteries.

Because it is possible that fibroblasts can become "activated" without displaying increased SMC α-actin, we also will probe sections for other fibroblast gene products. For example, we have antibodies for procollagen that stain cells producing collagen, in contrast to staining for mature forms of collagen for which staining is extracellular. We also have probes suitable for, and experience with, Northern, RNAse protection assays, quantitative PCR and in situ hybridization for markers including SMC α-actin, all FN isoforms and PAI-1.

Proliferation index. Animals, both treated and controls, will receive BrdU just prior to euthanasia. Tissue sections will be immunostained with an antibody against BrdU (Cappel) followed by fluorescently-labelled secondary antibodies. The total number of cells will be determined by Hoechst 33342 stain and from it the percentage of BrdU-positive cells will be calculated. The resulting data represents an "instantaneous" proliferation index. This "snapshot" differs from a continuous label approach in which BrdU would be infused for days rather than the 2 hrs called for in our protocol. Ki-67 immunolabelling will be used as an alternative method. In an earlier model, using anti-TGF-β, others noted a decreased cellularity in wound granulation tissue.

Apoptosis: In a healing wound, the number of fibroblasts and endothelial cells decrease markedly during the interval in which scar is maturing while fibroproliferative disorders have much lower apoptotic indices. An increase in the proportion of cells with a dot-like nuclear staining pattern (Hoechst-stained), as opposed to the more intact nuclear stain observed in healthy cells, will be indicative of increased apoptosis. To confirm that apoptotic pathways have been activated, Caspase-3 in tissue sections will also be stained for. We have a polyclonal antibody (PharMingen) that reacts preferentially with the active Caspase-3 in acetone-fixed frozen sections and will determine whether, and to what extent, fibroblast death increases as a function of Mab treatment. We will also determine if altered apoptotic frequencies occur for epidermal keratinocytes, endothelial cells, vascular smooth muscle cells and inflammatory cells in Mab-treated wounds.

Based on Applicants' work in vitro, animals treated with a Hic-5 antagonist in these experiments would be expected to have increased proliferation in myofibroblasts, decreased smooth muscle cell α-actin (SMCA) expression, decreased extracellular matrix (ECM) protein synthesis and deposition, and a reduction in tensile strength of collagen fibers in the wound.

Example 4

Experimental Plan for Determining Effects on Tumor Growth

The effects of Hic-5 antagonists on tumor growth are assessed in mice. Mice (C57BL strain) weighing 20 to 25 g are used, although any mouse tumor model known to those skilled in the art can be used. Tumor cells are H-59, a sub-line of mouse Lewis lung carcinoma cells, as described by Brodt, Cancer Res. 46:2442-2448, 1986. Tumors are induced in mice, by the subcutaneous injection of 2×105 cells on day zero. Mice are palpitated daily for the appearance of tumors at the site of injection. Once tumors are palpable, mice are divided into two groups of 10 mice. Intra-tumor injections of either sterile saline (controls) or Y27632 (30 mg/kg), Apocyanin (10 mg/kg) or Fe-TBAP (5 mg/kg) or 50 ul phosphate-buffered saline containing 20 ug Hic-5 siRNA is injected into wounds or into flanking dermis at daily intervals for the duration of the treatment period (18 days) (Treated) in saline, are done. Tumors are measured daily using calipers. In accordance with the animal protocol and regulations governing the use of animals in research, mice are sacrificed once tumor size reached 150 mm$^2$ For this reason, mice in the control group are all terminated on or around Day 18.

Tumor growth in mice treated with Hic-5 antagonists are significantly reduced, when compared to saline-treated controls. Comparison of the mean tumor size in the two groups, shows that tumors in Hic-5 antagonist treated mice are smaller than those in the controls at all times. In addition, there is no further growth of the tumors in Hic-5 antagonist-treated animals between Day 18 and 24, at which time the experiment is terminated.

What is claimed is:

1. A method for inhibiting or reversing a fibrotic disorder in a mammalian subject, the method comprising:
   administering a therapeutically effective amount of a Hic-5 siRNA that has the nucleotide sequence of SEQ ID NO:1 or SEQ ID NO:2.

* * * * *

UNITED STATES PATENT AND TRADEMARK OFFICE
CERTIFICATE OF CORRECTION

PATENT NO. : 8,420,614 B2
APPLICATION NO. : 12/527307
DATED : April 16, 2013
INVENTOR(S) : Van De Water et al.

Page 1 of 1

It is certified that error appears in the above-identified patent and that said Letters Patent is hereby corrected as shown below:

On the Title Page:

In the Assignee (73): Delete "Albany Medical College" and insert --Albany Medical College and The Research Foundation of State University of New York--

Signed and Sealed this
Twenty-seventh Day of August, 2013

Teresa Stanek Rea
*Acting Director of the United States Patent and Trademark Office*

SEQUENCE LISTING

```
<160> NUMBER OF SEQ ID NOS: 8

<210> SEQ ID NO 1
<211> LENGTH: 21
<212> TYPE: RNA
<213> ORGANISM: Homo sapiens

<400> SEQUENCE: 1
ggagcuggau agacugaugu u                                              21

<210> SEQ ID NO 2
<211> LENGTH: 21
<212> TYPE: RNA
<213> ORGANISM: Homo sapiens

<400> SEQUENCE: 2
ggaccagucu gaagauaagu u                                              21

<210> SEQ ID NO 3
<211> LENGTH: 20
<212> TYPE: DNA
<213> ORGANISM: Artificial
<220> FEATURE:
<223> OTHER INFORMATION: synthetic primer

<400> SEQUENCE: 3
gtacctgaac ccgtgttgct                                                20

<210> SEQ ID NO 4
<211> LENGTH: 20
<212> TYPE: DNA
<213> ORGANISM: Artificial
<220> FEATURE:
<223> OTHER INFORMATION: synthetic primer

<400> SEQUENCE: 4
gaacccgttg atgtccactt                                                20

<210> SEQ ID NO 5
<211> LENGTH: 20
<212> TYPE: DNA
<213> ORGANISM: Artificial
<220> FEATURE:
<223> OTHER INFORMATION: synthetic primer

<400> SEQUENCE: 5
gctagatcgg ttgcttcagg                                                20

<210> SEQ ID NO 6
<211> LENGTH: 20
```

```
<212> TYPE: DNA
<213> ORGANISM: Artificial
<220> FEATURE:
<223> OTHER INFORMATION: synthetic primer

<400> SEQUENCE: 6
gcggaagtca gagagtgagg                                        20

<210> SEQ ID NO 7
<211> LENGTH: 20
<212> TYPE: DNA
<213> ORGANISM: Artificial
<220> FEATURE:
<223> OTHER INFORMATION: synthetic primer

<400> SEQUENCE: 7
catggcctcc aaggagtaag                                        20

<210> SEQ ID NO 8
<211> LENGTH: 20
<212> TYPE: DNA
<213> ORGANISM: Artificial
<220> FEATURE:
<223> OTHER INFORMATION: synthetic primer

<400> SEQUENCE: 8
ggttggcaca gggtacttta                                        20
```